United States Patent [19]

Hubbell et al.

[11] Patent Number: 5,626,863

[45] Date of Patent: May 6, 1997

[54] PHOTOPOLYMERIZABLE BIODEGRADABLE HYDROGELS AS TISSUE CONTACTING MATERIALS AND CONTROLLED-RELEASE CARRIERS

[75] Inventors: Jeffrey A. Hubbell, Austin, Tex.; Chandrashekhar P. Pathak, Waltham; Amarpreet S. Sawhney, Newton, both of Mass.; Neil P. Desai, Los Angeles, Calif.; Jennifer L. Hill, Austin, Tex.

[73] Assignee: Board of Regents, The University of Texas System, Austin, Tex.

[21] Appl. No.: 379,848

[22] Filed: Jan. 27, 1995

Related U.S. Application Data

[60] Division of Ser. No. 22,687, Mar. 1, 1993, Pat. No. 5,410, 016, which is a continuation-in-part of Ser. No. 843,485, Feb. 28, 1992, abandoned.

[51] Int. Cl.$^6$ .............................. A61K 9/58; C08G 63/08
[52] U.S. Cl. .................. 424/426; 128/898; 424/489; 525/54.1; 525/54.2; 525/408; 525/413; 525/415; 514/772.1; 514/772.3; 514/773; 514/777; 528/354; 528/361
[58] Field of Search ........................... 424/426, 489; 514/772.1, 772.3, 773, 777; 525/54.1, 54.2, 408, 413, 415; 528/354, 361; 128/898; 427/399; 523/105, 112, 113, 114, 115

[56] References Cited

U.S. PATENT DOCUMENTS

| | | | |
|---|---|---|---|
| 3,640,741 | 2/1972 | Etes | 106/170 |
| 3,925,895 | 12/1975 | Kliment et al. | 32/15 |
| 3,960,150 | 6/1976 | Hussain et al. | 128/260 |
| 3,981,303 | 9/1976 | Higuchi et al. | 128/260 |
| 3,986,510 | 10/1976 | Higuchi et al. | 128/260 |
| 3,993,071 | 11/1976 | Higuchi et al. | 128/260 |

(List continued on next page.)

FOREIGN PATENT DOCUMENTS

| | | | |
|---|---|---|---|
| D. 195304 | 9/1986 | European Pat. Off. | C12N 9/96 |
| 0195304 | 9/1986 | European Pat. Off. | C12N 9/96 |
| 0354855 | 2/1990 | European Pat. Off. | A61K 009/12 |
| 0399441 | 11/1990 | European Pat. Off. | C09D 4/00 |
| 0466648 | 1/1992 | European Pat. Off. | D06P 1/38 |
| 2232839 | 1/1973 | Germany . | |
| 3716544 | 10/1987 | Germany | C11D 3/37 |
| 277454 | 4/1990 | Germany | C03C 17/28 |

(List continued on next page.)

OTHER PUBLICATIONS

Abraham, K. M., et al., "Dimensionally Stable MEEP–Based Polymer Electrolytes and Solid–State Lithium Batteries," Chem. Mater. 3:339–348 (1991).

Abuchowski, et al., "Alteration of Immunological Properties of Bovine Serum Albumin by Covalent Attachment of Polyethylene Glycol," J. Biol. Chem., 252(11):3578–3581 (1977).

(List continued on next page.)

*Primary Examiner*—Shelley A. Dodson
*Attorney, Agent, or Firm*—Patrea L. Pabst

[57] ABSTRACT

Hydrogels of polymerized and crosslinked macromers comprising hydrophilic oligomers having biodegradable monomeric or oligomeric extensions, which biodegradable extensions are terminated on free ends with end cap monomers or oligomers capable of polymerization and cross linking are described. The hydrophilic core itself may be degradable, thus combining the core and extension functions. Macromers are polymerized using free radical initiators under the influence of long wavelength ultraviolet light, visible light excitation or thermal energy. Biodegradation occurs at the linkages within the extension oligomers and results in fragments which are non-toxic and easily removed from the body. Preferred applications for the hydrogels include prevention of adhesion formation after surgical procedures, controlled release of drugs and other bioactive species, temporary protection or separation of tissue surfaces, adhering of sealing tissues together, and preventing the attachment of cells to tissue surfaces.

43 Claims, 9 Drawing Sheets

U.S. PATENT DOCUMENTS

| | | | |
|---|---|---|---|
| 4,076,800 | 2/1978 | Marsh et al. | 424/70 |
| 4,080,969 | 3/1978 | Casey et al. | 128/335.5 |
| 4,095,600 | 6/1978 | Casey et al. | 128/335.5 |
| 4,118,470 | 10/1978 | Casey et al. | 424/19 |
| 4,193,845 | 3/1980 | Kaetsu et al. | 435/182 |
| 4,194,066 | 3/1980 | Kaetsu et al. | 435/182 |
| 4,195,129 | 3/1980 | Fukui et al. | 435/182 |
| 4,226,938 | 10/1980 | Yoshida et al. | 435/176 |
| 4,272,617 | 6/1981 | Kaetsu et al. | 435/182 |
| 4,295,762 | 10/1981 | Slovinsky | 405/264 |
| 4,298,002 | 11/1981 | Ronel et al. | 128/260 |
| 4,310,397 | 1/1982 | Kaetsu et al. | 204/159.22 |
| 4,352,883 | 10/1982 | Lim | 435/178 |
| 4,376,839 | 3/1983 | Malin | 524/303 |
| 4,391,909 | 7/1983 | Lim | 435/178 |
| 4,409,331 | 10/1983 | Lim | 435/178 |
| 4,434,150 | 2/1984 | Azed et al. | 424/1.1 |
| 4,450,150 | 5/1984 | Sidman | 424/1.1 |
| 4,452,973 | 6/1984 | Casey et al. | 528/354 |
| 4,475,160 | 10/1984 | Churchill et al. | 318/568.16 |
| 4,511,478 | 4/1985 | Nowinski et al. | 210/691 |
| 4,512,910 | 4/1985 | Schmidle | 252/188.31 |
| 4,526,938 | 7/1985 | Churchill et al. | 525/415 |
| 4,533,445 | 8/1985 | Orio | 204/159.19 |
| 4,563,489 | 1/1986 | Urist | 424/426 |
| 4,605,622 | 8/1986 | Hasegawa et al. | 435/182 |
| 4,636,552 | 1/1987 | Gay et al. | 525/63 |
| 4,637,931 | 1/1987 | Schmitz | 424/426 |
| 4,650,488 | 3/1987 | Bays et al. | 623/12 |
| 4,655,777 | 4/1987 | Dunn et al. | 623/16 |
| 4,663,286 | 5/1987 | Tsang et al. | 435/178 |
| 4,689,293 | 8/1987 | Goosen et al. | 435/1 |
| 4,716,203 | 12/1987 | Casey et al. | 525/408 |
| 4,741,337 | 5/1988 | Smith et al. | 128/334 R |
| 4,741,872 | 5/1988 | De Luca et al. | 424/486 |
| 4,744,365 | 5/1988 | Kaplan et al. | 128/335.5 |
| 4,744,933 | 5/1988 | Rha et al. | 264/4.3 |
| 4,745,160 | 5/1988 | Churchill et al. | 525/415 |
| 4,749,620 | 6/1988 | Rha et al. | 428/402.2 |
| 4,774,178 | 9/1988 | Egerer et al. | 435/41 |
| 4,804,691 | 2/1989 | English et al. | 523/118 |
| 4,806,355 | 2/1989 | Goosen et al. | 424/424 |
| 4,808,399 | 2/1989 | Rypacek et al. | 424/2 |
| 4,826,945 | 5/1989 | Cohn et al. | 528/76 |
| 4,888,413 | 12/1989 | Domb | 424/78.17 |
| 4,889,722 | 12/1989 | Sheffield et al. | 424/450 |
| 4,891,263 | 1/1990 | Kotliar et al. | 428/225 |
| 4,913,903 | 4/1990 | Sudmann et al. | 424/426 |
| 4,916,193 | 4/1990 | Tang et al. | 525/413 |
| 4,921,934 | 5/1990 | Bixler et al. | 528/355 |
| 4,923,645 | 5/1990 | Tsang et al. | 424/497 |
| 4,925,677 | 5/1990 | Feijen | 424/484 |
| 4,933,430 | 6/1990 | Kessler et al. | 528/323 |
| 4,938,763 | 7/1990 | Dunn et al. | 604/891.1 |
| 4,942,035 | 7/1990 | Churchill et al. | 424/423 |
| 4,950,596 | 8/1990 | Cheng et al. | 435/94 |
| 4,957,744 | 9/1990 | della Valle et al. | 424/401 |
| 4,994,277 | 2/1991 | Higham et al. | 424/443 |
| 4,999,417 | 3/1991 | Domb | 528/271 |
| 5,049,138 | 9/1991 | Chevalier et al. | 604/265 |
| 5,061,281 | 10/1991 | Mares et al. | 623/11 |
| 5,108,755 | 4/1992 | Daniels et al. | 424/426 |
| 5,120,802 | 6/1992 | Mares et al. | 525/415 |
| 5,129,889 | 7/1992 | Hahn et al. | 604/265 |
| 5,135,751 | 8/1992 | Henry et al. | 424/426 |
| 5,153,002 | 10/1992 | McMullen | 424/473 |
| 5,185,408 | 2/1993 | Tang et al. | 525/415 |
| 5,206,303 | 4/1993 | Tse et al. | 525/319 |
| 5,219,564 | 6/1993 | Zalipsky et al. | 424/78.17 |
| 5,258,034 | 11/1993 | Furlong et al. | 623/23 |
| 5,270,400 | 12/1993 | Spinu | 525/411 |
| 5,278,201 | 1/1994 | Dunn et al. | 523/113 |
| 5,278,202 | 1/1994 | Dunn et al. | 523/113 |
| 5,318,780 | 6/1994 | Viegas | 424/427 |
| 5,324,775 | 6/1994 | Rhee et al. | 525/54.2 |
| 5,410,016 | 4/1995 | Hubbell et al. | 528/354 |
| 5,417,983 | 5/1995 | Nagase et al. | 424/487 |

FOREIGN PATENT DOCUMENTS

| | | | |
|---|---|---|---|
| 8089314 | 7/1980 | Japan | C08F 259/04 |
| 8111916 | 2/1981 | Japan | C08F 214/06 |
| 8122306 | 3/1981 | Japan | C08F 20/10 |
| 81142038 | 11/1981 | Japan | B29D 7/02 |
| 81151701 | 11/1981 | Japan | C08F 2/54 |
| 59184029 | 10/1984 | Japan | B60K 20/02 |
| 59191750 | 10/1984 | Japan | C08L 27/06 |
| 60127342 | 7/1985 | Japan | C08L 27/06 |
| 60-28950 | 7/1985 | Japan | D06M 13/20 |
| 62-115012 | 11/1985 | Japan | C08F 299/06 |
| 6132271 | 2/1986 | Japan | C12N 11/10 |
| 61-211372 | 9/1986 | Japan | C09D 3/727 |
| 63-199208 | 2/1987 | Japan | C08F 14/06 |
| 63-260972 | 4/1987 | Japan | C09J 3/14 |
| 62-129376 | 6/1987 | Japan | C09K 3/10 |
| 1145139 | 11/1987 | Japan | B32B 27/10 |
| 63-247036 | 10/1988 | Japan | B32B 27/30 |
| 1198943 | 8/1989 | Japan | E04B 1/64 |
| 1266123 | 10/1989 | Japan | C08G 59/40 |
| 2-238030 | 9/1990 | Japan | C08J 5/18 |
| 2298505 | 12/1990 | Japan | C08F 20/26 |
| 0374423 | 3/1991 | Japan | C08F 299/00 |
| 0361041 | 3/1991 | Japan | B32B 27/30 |
| 3-184555 | 8/1991 | Japan | A61L 27/00 |
| 3184555 | 8/1991 | Japan | A61L 27/00 |
| 3295645 | 12/1991 | Japan | B32B 27/36 |
| 3294835 | 12/1991 | Japan | G03B 21/62 |
| 0539465 | 2/1993 | Japan | C09J 7/02 |
| 0567475 | 3/1993 | Japan | H01M 10/40 |
| 8800237 | 1/1988 | WIPO | A61K 009/50 |
| WO91/10425 | 7/1991 | WIPO | A61K 9/50 |
| WO93/21266 | 4/1992 | WIPO | C08K 5/15 |
| WO91/10425 | 7/1992 | WIPO | A61K 9/50 |
| WO92/21354 | 12/1992 | WIPO | A61K 009/00 |
| WO93/17669 | 9/1993 | WIPO | A61K 9/50 |
| WO93/16687 | 9/1993 | WIPO | A61K 9/50 |
| WO94/03155 | 2/1994 | WIPO | A61K 009/10 |
| WO94/02517 | 2/1994 | WIPO | A61K 031/725 |

OTHER PUBLICATIONS

Amudenwari, et al., "Short–term biocompatability studies of hydrogel–grafted collagen copolymers," J. Biomed. Materials Res., 20:1103–1109 (1986).

Andrade et al., "Protein Adsorption and Materials Biocompatability: A Tutorial Review and Suggested Hypothesis," Advances in Polymer Science, published by Springer–Verlag Berlin Heidelberg, 1–63(1986).

Brosse, J. C., et al., "Polymerisation de monomeres organiques dans des plasmas froids–1, Polymerisation de monomeres acryliques deposes en couches minces," Eur. Polym. J., 19:381–385 (1983).

Buck, "Cell Surface Receptors for Extracellular Matrix Molecules," Ann. Rev. Cell Bio., 3;179–205 (1987).

Cerrai, P., et al., "Polyether–polyester block copolymers by non–catalysed polymerization of a e–caprolactone with poly(ethylene glycol)," Polymer, 30:338–343 (1989).

Hunter, S. K., et al., "Surface Modification of Polyurethane to Promote Long–Term Patency of Peritoneal Access Devices," Trans. Am. Soc. Artif. Intern. Organs 29:250–254 (1983).

Chiang, W–Y, et al., "Preparation and Properties of UV–Autocurable BTDA–Based Polyester Multiacrylates. I. Effects of Acrylic Functionality and Polyol Molecular Weight," J. App. Pol. Sci., 41:2971–2985 (1990).

Chun, et al., "Studies on Microbial Transformations XIX, Use of Immobilized Cells of Streptomyces Roseochromagenes for the 16 .alpha.Hydroxylation of Dehydroepiandrosterone" J. Appl. Microbiol., 27:505–509(1981).

Cohn, et al., "Biodegradable PEOPLA block copolymer," J. Biomed. Materials Research, 22(993–1009 (1988).

Coleman, et al., "Blood–materials interactions; the Minimum Interfacial free energy and the optimum polarapolar ratio hypothesis, J. Biomed. Materials Res., 16:381–398 (1982).

Darquy, et al., "Immunoisolation of pancreatic a cells by microencapsulation–an in vitro study," Diabetologia, 28:776–780 (1985).

Desai, et al., "The short–term blood biocompatability of poly(hydroxyethyl methacrylate–co–methyl methacrylate) in an in vitro flow system measured by digital videomicroscopy," J. Biomaterial Sci. Polymer Ed., 1(2):123–146 (1989).

Desai, et al., "Solution Technique to Incorporate Polyethylene Oxide and other Water–Soluble Polymers into Surfaces of Polymeric Biomaterials", Biomaterials, 12:144–153 (1991).

Desai, et al., "Surface Physical Interpenetrating Networks of Poly(ethylene terephthalate) and Poly(ethylene oxide) with Biomedical Applications,"Macramolecules, 25:226–232 (1992).

Desai, et al., "Surface Modifications of Polymeric Biomaterials for Reduced Thrombogenicity," J. Polym. Mater. Sci. Eng., 62:731–735 (1991).

Diamond, et al., "Synergistic effects of Interceed (Tc7) and heparin in reducing adhesion formation in the rabbit uterine hornmodel," Fertility and Sterility, 55(2):389–394 (1991).

Domb, et al., "Poly(anhydrides),3, Poly(anhydrides) Based on Aliphatic Aromatic Diacids," J. Macromolecules, 22:3200–3204 (1989).

Doody, et al., "Recombinant tissue plasminogen activator reduces adhesion formation in a rabbit uterine horn model," Fertility and Sterility, 51(3):509–512 (1989).

Dunn, et al., "Synergistic Effect of Intraperitoneally administered calcium channel blockade and recombinant tissue plasminogen activator to prevent adhesion formation in an animal model," Am. J. Obstet. and Gynecol., 164(5):1327–1330 (1991).

Dupuy, et al., "In situ polymerization of a microencapsulating medium round living cells," J. Biomedical Materials Research, 22:1061–1070 (1988).

Dupuy, et al., "Microencapsulation of Isolated pituitary cells by polyacrylamide microlatex coagulation on agarose beads," Biomaterials, 12:493–496 (1991).

Eaton, "Dye Sensitized Photopolymerization," Advances in Photochemistry, 13:427–481 (1986).

Epaillard, et al., "Plasma Induced Polymerization," J. Applied Polymer Sci., 38:887–898 (1989).

Epaillard, et al., "Polymerisation induite par un plasma froid, Etude des mecanismes de polymerisation en gonction do l'epaisseur du film,"Makromol. Chem., 189:1035–1042 (1988).

Fouassier, et al., "Polymerization induite sous irradiation laser visible, 4–Le Systeme eosinePhotoamorceur Ultra–VioletAmine," Makromol. Chem., 192:245–260 (1991).

Fuertges, et al., "The Clinical Efficacy of Poly(Ethylene Glycol)Modified Proteins," J. Controlled Release, 11:139–148 (1990).

Nojiri, Chisato, et al., "Invivo Protein Adsorption onto Polymers: A Transmission Electron Microscopic Study," Trans Am. Soc. Artif. Intern. Organs 35:357–361 (1989).

Fukui, et al., "°Entrapment of Biocatalysts with Photo–Cross–Linkable Resin Prepolymers and Urethane Resin Prepolymers," Methods in Enzymology, 135:230–252 (1987).

Fukui, et al., "Application of Photo–Crosslinkable Resin to immobilization of an Enzyme," FEBS Letters, 66(2):179–182 (1976).

Fukui, et al., "Application of Biocatalysts Immobilized by Prepolymer Methods," Advances in Mechanical Engineering and Biotechnology, 29:1–33 (1984).

Gabbay et al., "New Outlook on Pericardial Substitution After Open Heart Operations," Ann. Thorac. Surg., 48:803–812 (1989).

Gharapetian, et al., "Encapsulation of Viable Cells Within Polyacrylate Membranes," Biotechnology and Bioengineering, 28:1595–1600 (1986).

Gharapetian, et al., "Polyacrylate Microcapsules for Cell Encapsulation: Effects of Copolymer Structure on Membrane Properties," Biotechnology and Bioengineering, 30:775–779 (1987).

Gibble, et al., "Fibrin glue: the perfect operative sealant?," Transfusion, 30(8):741–747 (1990).

Gin, et al., "Agarose encapsulation of Islets of Langerhans: reduced toxicity in vitro," J. Microencapsulation, 4(3):239–242 (1987).

Golander, C–G. et al., "Preparation and Protein Adsorption Properties of Photopolymerized Hydrophilic Films Containing N–Vinylpyrrolidone (NVP), Acrylic Acid (AA) or Ethyleneoxide (EO) Units as Studies by ESCA,"Colloids and Surfaces, 21:149–165 (1986).

Goldberg, et al., "An Evaluation of the Gore–Tex Surgical Membrane for the Prevention of Postoperative Peritoneal Adhesion," Obstetrics and Gynecology, 70(6):846–848 (1987).

Gombotz, et al., "Immobilization of Poly(ethylene Oxide) on Poly(ethylene Terephthalate) Using a Plasma Polymerization Process," J. Applied Polymer Science, 37:91–107 (1989).

Goosen, et al., "Optimization of Microencapsulation Parameters Semipermeable Microcapsules as a Bioartificial Pancreas," Biotech. and Bioeng., 27:146–150 (1985).

Graham, N. B. and McNeill, M. E., "Hydrogels for controlled drug delivery,"Biomaterials, 5:27–36 (19894).

Harris, "Laboratory Synthesis of Polyethylene Glycol Derivtives," Macromol. Chem. Phys., C25(3):325–373 (1985).

Hattori, et al., "Fibroblast Cell Proliferation on Charged Hydroxyethyl Methacrylate Copolymers, J. Colloid and Interface Science, 104(1):72–78 (1985).

Heller, J. et al., "Controlled Release of Water–soluble Macromolecules from Bioerodible Hydorgels," Biomaterials, 262–266 (1983).

Heller, et al., "Poly(ortho enters)," Biodegradable Polymers as Drug Delivery System, Chasin and Langer eds., 121–161 (1990).

Holland, et al., "Polymers for Biodegradable Medical Devices, 1, The Potential of Polyesers as Controlled Macromolecular Release Systems," J. Controlled Release, 4:155–180 (1986).

Holtz, "Prevention and Management of Peritoneal Adhesions," Fertility and Sterility, 42(4):497–507 (1984).

Horbett, "Mass Action Effects on Competitive Adsorption of Fibrinogen from Hemoglobin Solutions and from Plasma," rhromb. Haomostas, (Stuttgart), 51(2):174–181 (1984).

Hu, D., et al., H–S. "Effect of soft segment on degradation kinetics in polyethylene glycolpoly(L–lactide) block copolymers," Polymer Bulletin, 30:669–676 (1993).

Huffman, et al., Effect of Carbosyl End Groups on Hydrolysis of Polyglycolic Acid," J. Polymer Science, Polymer Chemistry Edition, 23:1939–1951 (1985).

Hunt, et al., "Synthesis and Evaluation of a Prototypal Artificial Red Cell," Science, 6:1165–1168 (1985).

Interceed (TC7) Adhesion Barrier Study Group, "Prevention of postsurgical adhesions by Interceed (TC7), an absorbable adhesion barrier: a prospective randomized multicenter clinical study," Fertility and Sterility, 51(6):933–938 (1989).

Itoh, T., et al., "Development of Novel Photocurable Medical–Use Resins: Molecular Design a Considerations and Basic Properties," Jap. J. Artif. Organs, 18(1):132–136 (1989).

Iwata, et al., "Evaluation of Microencapsulated Islets In Agarose Gel as Bioartificial Pancreas by Studies of Hormone Secretion in Culture and by Xenotransplantation," Diabetes, 38(1):224–225 (1989).

Kanako, K., et al., CA 84:123221a, "Radiation–induced graft copolymerization to polyester, XVII, Grafting of polyethylene glycol dimethacrylates and diacrylates onto poly-(ethylene terephthalate) fabric with electron beams," Nippon Genshiryoky Kenkyusho Nempo, 5030, 48–59 (1975).

Karel, S. F., et al., "The Immobilization of Whole Cells: Engineering Principles," Chem. Eng. Sci., 40(8):1321–1354 (1985).

Karu, "Yearly Review–Effects of Visible Radiation on Cultured Cells,"Photochemistry and Photobiology, 52(6):1089–1098 (1990).

Kenley, et al., "Poly(lactide–co–glycolide) Decomposition Kinetics in vivo and in vitro," Macromolecules, 20:2398–2403 (1987).

Kimura, et al., "Some Properties of an Immobilized Glycolysis System of Yeast In Fermentative Phosphorylation of Nucleotides," European J. Appl. Microbiol. Biotechnol., 11:78–80 (1981).

Kimura, et al., "Immobilization of Glycolysis System of Yeasts and Production of Cytidine Diphosphate Choline," Eur. J. Microbiol. Biotechnol., 5:13–16 (1978).

Koshiba, M., et al., "Properties of Ultra–Violet Curable Polyurethane Acrylates," J. Materials Sci., 17:1447–1458 (1982).

Kricheldorf, H. R. et al., "ABA Triblock Copolymers of L–Lactide and Poly(ethylene glycol)," Makromol. Chem., 194:715–725 (1993).

Kulkarni, et al., "Biodegradable Poly(lactic acid) Polymers," J. Biomed. Mater. Res., 5:169–181 (1971).

Kulkarni, et al., "Polylactic Acid for Surgical Implants," Arch. Surg., 93:841–845 (1966).

Kumakura, M., et al., "Immobilization of Microbial Cells in Membrane Form by Radiation–Induced Cast–Polymerization," Die Angewandte Makromol. Chemie., 115:75–86 (1983).

Lamberti, et al., "Microencapsulation of Mammalian Cells in Polyacrylates,"Applied Biochem. and Biotech., 10:101–104 (1984).

Leach, et al., "Reduction of postoperative adhesions in the rat uterine horn modal with poloxamer 407," Am. J. Obstet. Gynecol., 162(5):13171319 (1990).

Lin, M–S., et al., "Optically Clear Simultaneous Interpenetrating Polymer Networks Based on Poly(ethylene glycol) Diacrylate and Epoxy.I. Preparation and Characterization," J. Polymer Sci., 30:1941–1951 (1992).

Lipstova, "Medical Polymer Adhesives," Advances in Polym. Sci., 79:65–92 (1986).

Matsuda, T., et al., "Photoinduced Prevention of Tissue Adhesion," Asaio Transactions, 38:M154–M155 (1992).

Mayer, et al., "Effect of viscous macromolecules on peritoneal plasminogen activator activity; A potential mechanism for their ability to reduce postoperative adhesion formation," Am. J. Obstet. Gynecol., 159(4):957–963 (1988).

McMahon et al., Feasibility of Cellular Microencapsulation Technology for Evaluation of Anti–Human Immunodeficiency Virus Drugs in vivo," J. of the Nat'l Cancer Institute, 82(22):1761–1765 (1990).

Menzies, et al., "The Role of Plasminogen Activator in Adhesion Prevention," Surgery, Gynecology and Obstetr., 172:362–366 (1991).

Merrill, E. W., et al., "Platelet–Compatible Hydrophilic Segmented Polyurethanes From Polyethylene Glycols and Cyclohexane Diisocyanate,"Trans. Am. Soc. Artif. Intern. Organs, 28:482–487 (1982).

Miller, et al., "Degradation Rates of Oral Resorbable Implants (Polylactates and Polyglycolates); Rate Modification with Changes in PLAPGA Copolymer Ratio," J. Biomed. Mater. Res., 11:711–719 (1977).

Miyama, H., et al., "Graft Copolymerization of Methoxypoly(ethylene glycohol) Methacrylate onto Polyacrylonitrile and Polyacrylonitrile and Evaluation of Nonthrombogenicity of the Copolymer," J. Applied Polymer Sci., 35:115–125 (1988).

Miyake, et al., "Solution Properties of Synthetic Polypeptides, XVIII; Helix–Coil Transition of Poly–m2(2–Hydroxyethyl)L–Glutamine," Biopolymers, 13:1173–1186 (1974).

Mori, Y., et al., "A New Antithrombogenic Material with Long Polyethyleneoxide Chains," Trans. Am. Soc. Artif. Intern. Organs, 28:459–463 (1982).

Nagaoka, et al., "Interaction Between Blood Components and Hydrogels with Poly(Oxyethylene) Chains", in Polymers as Biomaterials, Shalaby & Shalaby, ed. Plenum Press, New York and London, 361–374 (1984).

Neckers, et al., "Photopolymerization Using Derivatives of Fluorescein,"Polym. Materials Sci. Eng., 60:15–16 (1989).

Okada, et al., "Application of Entrapped Growing Yeast Cells to Peptide Secretion System", Appl. Microbiol. Biotechnol., 26:112–116 (1987).

Omata, et al., "Stereoselective Hydrolysis of dl–Menthyl Succinate by Gel–Entrapped Rhodetoe–u,La minuta var. texonsis Cells in Organic Solvent," European J. Appl. Microbiol. Biotechnol., 199–204 (1981).

Omata, et al., "Immobilization of Microbial Cells and Enzymes with Hydrophobic Photo–Crosslinkable Resin Prepolymers," Eur. J. Appl. Microbio. Biotechnol., 6:207–215 (1979).

Omata, et al., "Transformation of Steroids by Gel–Entrapped Micardia rhodocrous Cells in Organic Solvent," Eur. J. Appl. Microbiol. Biotechnol., 8:143–155 (1979).

Oshea, et al., "Encapsulation of Rat Islets of Langerhans Prolongs Xenograft Survival in Diabetic Mice," Diabetes, 35:943–946 (1986).

Pagidas, et al., "Effect of Ringer's Lactate, Interceed (TC7) and Gore-Tex Surgical membrane on Postsurgical Adhesion Formation," Fertility and Sterility, 57(I):199–201 (1992).

Park, et al., "Immobilization of Arthrobactor–Simplex Cells in Thermally Reversible Hydrogels Comparative Effects of Organic Solvent and Polymeric Surfactant on Steroid Conversion," Biotechnology Letters, 11(I):17–22 (1989).

Peterson, R. G., "Polyethylene Glycol Diacrylates as Embedding Media for Electron Microscopy," Thirteenth Annual Meeting, Electron Microscopy Society of America and First Pacific Regional Conference on Electron Microscopy, 144–145 (1972).

Philips, M., et al., "Radiation curable water dilutable polyester acrylates," European Polymers Paint Colour J., 183(4322):38–40 (Feb. 10, 1993).

Pitt, et al., "Aliphatic Polyesters, 1, The Degradation of Poly(caprolactone)in vivo," J. Applied Polymer Science, 26:3779–3787 (1981).

Pitt, et al., "Aliphatic polyesters II, The degradation of poly(DL–lactide), poly (caprolactone), and their copolymers in vivo,"Biomaterials, 2:215–220 (1981).

Priola, A., et al., "Investigation on the structure–property relationships for films obtained from UV curable coatings," Progress in Organic Coatings, 22:301–314 (1993).

Priola, A., et al., "Properties of polymeric films obtained from u.v. cured poly(ethylene glycol) diacrylates," Polymer. 34(17):3653–3657 (1993).

Punnonen, et al., Polyethylene glycol 4000 in the prevention of peritoneal adhesions," Fertility and Sterility, 38(4):491–492 (1982).

Ratzsch, M., et al.,"Strahlkenchische Antielektrostatik–Austrustung," Acta Polymerica, 41:453–460 (1990).

Rempp, et al., "Anionically Polymerized Star Macromolecules Having Divinyl Benzene Cores with Grafted Poly-(Ethylene oxide) Arms as Biomaterials,"Abstract, Polymer Preprints, 31(1):215 (1990).

Reuveny, et al., "Factors Affecting Cell Attachment, Spreading, and Growth on Derivatized Microcarriers, 1. Establishment of Workingg System and Effect of the Type of the Amino–Charged Groups," Biotechnology and Bioengineering, 25:469–480 (1983).

Sawhney, et al., "Rapidly degraded terpolymers of dl–lactide, glycolide, and a–caprolactone with increased hydrophilicity by copolymerization with polyethers," J. Biomedical Materials Research, 24:1397–1411 (1990).

Skarda, V., et al., "Biodegradable Hydrogel for Controlled Release of Biologically Active Macromolecules," J. Bioactive and Compatible Polymers, 8:24–37 (1993).

Sefton et al., "Hydrophilic Polyacrylates for the Microencapsulation of Fibroblasts or Pancreatic Islets," J. Controlled Release, 6:177–187 (1987).

Shimizu, Y., et al., "Studies on Composites of Collagen and a Synthetic Polymer," Biomat. Med. Dev. Art. Org., 6(4):375–391.

Sonomoto, K., et al., "Growth of Curvularia lunata spores into mycelial form within various gels, and steroid 11β–hydroxylation by the entrapped mycelia," J. Ferment. Technol., 59(6):465–469 (1981).

Speckhard, T. A., et al., "Properties of UV–Curable Polyurethane Acrylates: Effect of Reactive Diluent," J. Appl.Poly. Sci., 30:647–666 (1985).

Spilizewski, et al., "The Effect of Hydrocortisone Acetate Loaded Poly(DL–lactide) Films on the Inflammatory Response," J. Controlled Release, 2:197–2032 (1985).

Steinleitner, et al., "Poloxamer 407 as an Intraperitoneal Barrier material for the Prevention of Postsurgical Adhesion Formation and Reformation in Rodent Models for Reproductive Surgery," Obstetrics and Gynecologgy, 77(1):48–52 (1991).

Stevenson, et al., "Graft copolymer emulsions of sodium alginate with hydroxyalkyl methacrylates for microencapsulation," Biomaterials, 8:449–457 (1987).

Sun, et al., "Non–fouling Biomaterial Surfaces: II, Protein Adsorption on Radiation Grafted Polyethylene Glycol Methacrylate Copolymers," Polymer Preprints, 28(1):29214 294 (1987).

Suzuki, et al., "Microencapsulation and Dissolution Properties of a Neuroleptic in a Biodegradable Polymer, Poly(d, l–lactide), J. Pharmaceutical Sciences, 74(I)20–24 (1985).

Tanaka, et al., "Immobilization of Yeast Microbodies by Inclusion with Photo–Crosslinkable Resins," Eur. J. Biochem., 80:193–197 (1977).

Thompson, et al., "Fibrin Glue: A Review of its Preparation Efficacy, and Adverse Effects as a Topical Hemostat," Drug Intelligence and Clinical Pharmacy, 22:946–952 (1988).

Tulandi, et al., "Treatment–dependent and tretment–independent pregnancy among women with periadnexal adhesions," Am. J. Obstet. Gynecol., 162(2):354–357 (1990).

Uretzky, G., et al., "Long–term evaluation of a new selectively biodegradable vascular graft coated with polyethylene oxide–polylactic acid for right ventricular conduit," J. Thorac Cardiovasc. Surg., 133:769–780 (1990).

Urman, et al., "Effect of hyaluronic acid on postoperative intraperitoneal adhesion formation and reformation in the rat model," Fertility and Sterility, 56(3):568–570 (1990).

Urman, et al., "Effect of hyaluronic acid on postoperative intraperitoneal adhesion formation in the rat model," Fertility and Sterility, 56(3):563–567 (1991).

van Neerbos, A., "Parameters in UV Curable Materials Which Influence Cure Speed," J. Oil Col. Chem. Assoc., 61:241–250 (1978).

Van Wachom, et al., "Adhesion of cultured human endothelial cells onto methacrylate polymers with varying surface wettability and charge,"Biomaterials, 8:323–328 (1987).

Viescher, et al., "Biodegradation of and tissue reaction to 50:50 poly(DL–lactide–co–glycolide) microcapsules," J. Biomedical Materials Research, 19:349–365 (1985).

Wen et al., "Microcapsules through Polymer Complexation," Dept. of Chemistry and Inst. for Aviation Research (1990).

Wong, et al., "The Viability and Regeneration of Artificial Cell Microencapsulated Rat hepatocyte Xenograft Transplants in Mice," Biomat., 16(4):731–739 (1988).

Woodward, et al., "The intracellular degradation of poly(c–caprolactone),"J. Biomedical Materials Research, 19:437–444 (1985).

Wu, "Optical–scanner Design Impacts Rapid Laser Prototyping," Laser Focus World, 99–106 (Nov. 1990).

Wujek, et al., "A Carbohydrate Polymer that Effectively Prevents Epidural Fibrosis at Laminectomy sites in the Rat," Exp. Neurology, 114:237–245 (1991).

Sun, Anthony M., "Encapsulated Versus Modified Endocrine Cells for Organ Replacement," Trans. Am. Soc. Artif. Intern. Organs 33:787–790 (1987).

Crooks, Colin A., et al., "Microencapsulation of mammalian cells in a HEMA–MMA copolymer: Effects on capsule morphology and permeability,"Journal of Biomedical Materials Research 24:1241–1262 (1990).

Altman, J. J., et al., "Long–Term Plasma Glucose Normalization in Experimental Diabetic Rats With Microencapsulated Implants of Benign Human Insulinomas," Diabetes 35:625–633.

Iwata, et al., "The Use of Photocrosslinkable Polyvinyl Alcohol in the Immunoisolation of Pancreatic Islets," Transplantation Proceedings 22(2):797–799 (Apr. 1990).

Fukui, et al., "Several novel methods for immobilization of enzymes, microbial cells and organelles," Biochimie 62:381–386 (1980).

King, G. A., et al., "Alginate–Polylysine Microcapsules of Controlled Membrane Molecular Weight Cutoff for Mammalian Cell Culture Engineering,"Biotechnology Progress 3(4):231–240 (Dec., 1987).

Lacy, Paul E., et al., "Maintenance of Normoglycemia in Diabetic Mice by Subsutaneous Xenografts of Encapsulated Islets," Science 254:1782–1794 (1991).

Lee, Jin Ho, et al., "Protein–resistant surfaces prepared by PEO–containing block copolymer surfactants," Journal of Biomedical Materials Reserch 23:351–368 (1989).

Maechling–Strasser, C., et al., "Preadsorption of polymers on glass and silica to reduce fibrinogen adsorption," Journal of Biomedical Materials Research 23:1385–1393 (1989).

Mallabone, C. L., et al., "Microencapsulation of human diploid fibroblasts in cationic polyacrylates," Dept. of Chem. Eng. and Applied Chem. and Centre for Biomaterials (1989).

Nagaoka, Shoji and Akimass Nakao, "Clinical application of antithrombogenic hydrogel with long poly(ethylene oxide) chains," Biomaterials 11:119–121 (1990).

Reach, Gerard, et al., "A U–Shaped Bioartificial Pancreas with Rapid Glucose–Insulin Kinetics," Diabetes 33:752–761 (1984).

Ronel, Samuel H., et al., "Macroporous hydrogel membranes for a hybrid artificial pancrease, I. Synthesis and chamber fabrication," Journal of Biomedical Materials Research 17:855–864 (1983).

Sawhney, Amarpreet S. and Jeffrey A. Hubbell, "Poly(ethylene oxide)–graft–poly(L–lysine) copolymers to enhance the biocompatibility of poly(L–lysine)–alginate microcapsule membranes," Biomaterials 13(12):863–870 (1992).

Stevenson, W. T. K., et al., "Microencapsulation of Mammalian Cells in a Hydroxyethyl Methacrylate–Methyl Methacrylate Copolymer," Biomat. Art. Cells. Art. Org. 16(4):747–769 (1988).

Fukuzaki, Hironobu, et al., "A new biodegradable copolymer of glycolic acid and lactones with relatively low molecular weight prepared by direct copolycondensation in the absence of catalysts," J. of Bio. Materials Research 25:315–328 (1991).

Lim, F., and Sun, A., "Microencapsulated Islets as Bioartificial Endocrine Pancreas," Science, 210:908–910.

Sawhney, A. S., Pathak, C. P. and Hubbell, J. A., "Bioerodible Hydrogels Based on Photopolymerized Poly(ethylene glycol)–co–poly(a–hydroxy acid) Diacrylate Macromers," Macromolecules, 26:581–587 (1993).

Desai and Hubbell, "Surface Modifications of Polymeric Biomaterials for Reduced Thrombogenicity," Polymeric Materials Science and Engineering, Proceedings of the ACS Division of Polymeric Materials Science and Engineering, 62:731–735 (1990).

Zhu, K. J., et al., "Preparation and Properties of D,L–Lactide and Ethylene Oxide Copolymer: A Modifying Biodegradable Polymeric Material," J. Polymer Sci., Part C: Polymer Letters, 24:331–337 (Aug. 1986).

Zhu, K. J., et al., "Preparation, Characterization and Properties of Polylactide (PLA)–Poly(ethylene Glycol) (PEG) Copolymers: A Potential Drug Carrier," J. Applied Polymer Sci., 39:1–9 (Feb. 1990).

Zhu, K. J., et al., "Super Microcapsules" (SMC), I. Preparation and Characterization of Star Polyethylene Oxide (PEO)–Polylactide (PLA) Copolymers," J. Polymer Sci: Part A: Polymer Chemistry, 27:2151–2159 (Sep. 1989).

PHOTOPOLYMERIZABLE BIODEGRADABLE HYDROGELS AS TISSUE CONTACTING MATERIALS AND CONTROLLED-RELEASE CARRIERS

BACKGROUND OF THE INVENTION

This is a divisional of application U.S. Ser. No. 08/022,687 filed in the U.S. Patent & Trademark Office on Mar. 1, 1993, now U.S. Pat. No. 5,410,016 entitled 'Photopolymerizable Biodegradable Hydrogels as Tissue Contacting Materials and Controlled-Release Carriers' which is a continuation-in-part of U.S. patent application No. 07/843,485, filed Feb. 28, 1992, now abandoned entitled "Photopolymerizable Biodegradable Hydrogels as Tissue Contacting Materials and Controlled Release Carriers" by Jeffrey A. Hubbell, Chandrashekhar P. Pathak, and Amarpreet S. Sawhney.

FIELD OF THE INVENTION

The present invention relates to photopolymerizable biodegradable hydrogels for use as tissue adhesives and in controlled drug delivery.

Hydrogels as controlled-release carriers

Biodegradable hydrogels can be carriers for biologically active materials such as hormones, enzymes, antibiotics, antineoplastic agents, and cell suspensions. Temporary preservation of functional properties of a carried species, as well as controlled release of the species into local tissues or systemic circulation, are possible. Proper choice of hydrogel macromers can produce membranes with a range of permeability, pore sizes and degradation rates suitable for a variety of applications in surgery, medical diagnosis and treatment.

Adhesives and sealers

Fibrin gels have been used extensively in Europe as sealants and adhesives in surgery (Thompson et al., 1988, "Fibrin Glue: A review of its preparation, efficacy, and adverse effects as a topical hemostat," *Drug Intell. and Clin. Pharm.*, 22: 946; Gibble et al., 1990, (1990), "Fibrin glue: the perfect operative sealant?" *Transfusion*, 30(8): 741). However, they have not been used extensively in the United States due to concerns relating to disease transmission from blood products. Synthetic polymers have been explored as adhesives (Lipatova, 1986, "Medical polymer adhesives," *Advances in Polymer Science* 79: 65–93), but these materials have been associated with local inflammation, cytotoxicity, and poor biocompatibility.

Prevention of postoperative adhesions.

Formation of post-surgical adhesions involving organs of the peritoneal cavity and the peritoneal wall is a frequent and undesirable result of abdominal surgery. Surgical trauma to the tissue caused by handling and drying results in release of a serosanguinous (proteinaceous) exudate which tends to collect in the pelvic cavity (Holtz, G., 1984). If the exudate is not absorbed or lysed within this period it becomes ingrown with fibroblasts, and subsequent collagen deposition leads to adhesion formation.

Numerous approaches to elimination of adhesion formation have been attempted, with limited success in most cases. Approaches have included lavage of the peritoneal cavity, administration of pharmacological agents, and the application of barriers to mechanically separate tissues. For example, Boyers et al., (1988) "Reduction of postoperative pelvic adhesions in the rabbit with Gore-Tex surgical membrane," *Fertil. Steril.*, 49: 1066, examined Gore-Tex surgical membranes in the prevention of adhesions. For a review of adhesion prevention, see Holtz (1984) "Prevention and management of peritoneal adhesions," *Fertil. Steril.*, 41: 497–507. However, none of these approaches has been cost effective and effective in in vivo studies.

Solutions of Poloxamer 407 have been used for the treatment of adhesions, with some success. Poloxamer is a copolymer of ethylene oxide and propylene oxide and is soluble in water; the solutions are liquids at room temperature. Steinleitner et al. (1991) "Poloxamer 407 as an Intraperitoneal Barrier Material for the Prevention of Postsurgical Adhesion Formation and Reformation in Rodent Models for Reproductive Surgery," *Obstetrics and Gynecology*, 77(1):48 and Leach et al. (1990) "Reduction of postoperative adhesions in the rat uterine horn model with poloxamer 407, *Am. J. Obstet. Gynecol.*, 162(5): 1317, examined Poloxamer solutions in peritoneal adhesion models and observed statistically significant reductions in adhesions; however, they were unable to eliminate adhesions, perhaps because of limited adhesion and retention on the injury site.

Oxidized regenerated cellulose has been used extensively to prevent adhesions and is an approved clinical product, trade-named Interceed TC7. This barrier material has been shown to be somewhat effective in rabbits (Linsky et al., 1987 "Adhesion reduction in a rabbit uterine horn model using TC-7," *J. Reprod. Med.*, 32: 17; Diamond et al., 1987 "Pathogenesis of adhesions formation/reformation: applications to reproductive surgery," Microsurgery, 8: 103) and in humans (Interceed (TC7) Adhesion Barrier Study Group, 1989). It was shown to be more effective if pretreated with heparin, but was still unable to completely eliminate adhesions (Diamond et al., 1991 "Synergistic effects of INTERCEED(TC7) and heparin in reducing adhesion formation in the rabbit uterine horn model," *Fertility and Sterility*, 55(2): 389).

In summary, several lavage/drug/material approaches have been explored, but none of these approaches has been able to eliminate adhesions. An ideal material barrier would not evoke an adhesion response itself, stay in place without suturing (Holtz et al., 1982 "Adhesion induction by suture of varying tissue reactivity and caliber," *Int. J. Fert.*, 27: 134), degrade over a few weeks' time, effectively reduce adhesions to very low extent, and be capable of delivering a drug to the local site of application for several days' time. None of the approaches developed and described to date meet these requirements.

Synthetic biodegradable polymers

The field of biodegradable polymers has developed rapidly since the synthesis and biodegradability of polylactic acid was first reported by Kulkarni et al., 1966 "Polylactic acid for surgical implants," *Arch. Surg.*, 93: 839. Several other polymers are known to biodegrade, including polyanhydrides and polyorthoesters, which take advantage of labile backbone linkages, as reported by Domb et al., 1989 *Macromolecules*, 22: 3200; Heller et al., 1990 *Biodegradable Polymers as Drug Delivery Systems*, Chasin, M. and Langer, R., Eds., Dekker, New York, 121–161. Since it is desirable to have polymers that degrade into naturally occurring materials, polyaminoacids have been synthesized, as reported by Miyake et al., 1974, for in vivo use. This was the basis for using polyesters (Holland et al., 1986 Controlled Release, 4: 155–180) of α-hydroxy acids (viz., lactic acid, glycolic acid), which remain the most widely used biodegradable materials for applications ranging from closure devices (sutures and staples) to drug delivery systems (U.S. Pat. No. 4,741,337 to Smith et al.; Spilizewski et al., 1985

"The effect of hydrocortisone loaded poly(dl-lactide) films on the inflammatory response," *J. Control. Rel.* 2: 197–203).

The time required for a polymer to degrade can be tailored by selecting appropriate monomers. Differences in crystallinity also alter degradation rates. Due to the relatively hydrophobic nature of these polymers, actual mass loss only begins when the oligomeric fragments are small enough to be water soluble. Hence, initial polymer molecular weight influences the degradation rate.

Degradable polymers containing water-soluble polymer elements have been described. Sawhney et al., (1990) "Rapidly degraded terpolymers of dl-lactide, glycolide, and $\epsilon$-caprolactone with increased hydrophilicity by copolymerization with polyethers," *J. Biomed. Mater. Res.* 24: 1397–1411, copolymerized lactide, glycolide and $\epsilon$-caprolactone with PEG to increase its hydrophilicity and degradation rate. U.S. Pat. No. 4,716,203 to Casey et al. (1987) synthesized a PGA-PEG-PGA block copolymer, with PEG content ranging from 5–25% by mass. U.S. Pat. No. 4,716,203 to Casey et al. (1987) also reports synthesis of PGA-PEG diblock copolymers, again with PEG ranging from 5–25%. U.S. Pat. No. 4,526,938 to Churchill et al. (1985) described noncrosslinked materials with MW in excess of 5,000, based on similar compositions with PEG; although these materials are not water soluble. Cohn et al. (1988) *J. Biomed. Mater. Res.* 22: 993–1009 described PLA-PEG copolymers that swell in water up to 60%; these polymers also are not soluble in water, and are not crosslinked. The features that are common to these materials is that they use both water-soluble polymers and degradable polymers, and that they are insoluble in water, collectively swelling up to about 60%.

Degradable materials of biological origin are well known, for example, crosslinked gelatin. Hyaluronic acid has been crosslinked and used as a degradable swelling polymer for biomedical applications (U.S. Pat. No. 4,987,744 to della Valle et al., U.S. Pat. No. 4,957,744 to Della Valle et al. (1991) "Surface modification of polymeric biomaterials for reduced thrombogenicity," *Polym. Mater. Sci. Eng.*, 62: 731–735]).

Use of biodegradable materials for controlled drug release

Most hydrophilic drugs are mechanically dispersed as suspensions within solutions of biodegradable polymers in organic solvents. Protein and enzyme molecular conformations are frequently different under these circumstances than they would be in aqueous media. An enzyme dispersed in such a hydrophobic matrix is usually present in an inactive conformation until it is released into the surrounding aqueous environment subsequent to polymer degradation. Additionally, some proteins may be irreversibly denatured by contact with organic solvents used in dispersing the protein within the polymer.

Polymer synthesis, degradation and local synthesis

Rapidly-degrading polymers currently suggested for short-term macromolecular drug release may raise local concentrations of potentially hazardous acidic degradation byproducts. Further, all biodegradable synthetic polymers reported thus far can only be processed in organic solvents and all biodegradable polymers are synthesized under conditions which are not amenable to polymerization in vivo. Thus, it has not been possible to make implantable materials as precisely conformed barriers, shaped articles, or membranes capable of delivering bioactive materials to the local tissue.

It is therefore an object of the present invention to provide hydrogels which are biocompatible, biodegradable, and can be rapidly formed by polymerization in vivo.

It is a further object of the present invention to provide a macromer solution which can be administered during surgery or outpatient procedures and polymerized as a tissue adhesive, tissue encapsulating medium, tissue support, or drug delivery medium.

It is a still further object of the present invention to provide a macromer solution which can be polymerized in vivo in a very short time frame and in very thin, or ultrathin, layers.

SUMMARY OF THE INVENTION

Disclosed herein are biocompatible, biodegradable, polymerizable and at least substantially water soluble macromers, having a variety of uses in vivo. The macromers include at least one water soluble region, at least one region which is biodegradable, usually by hydrolysis, and at least two free radical-polymerizable regions. The regions can, in some embodiments, be both water soluble and biodegradable. The macromers are polymerized by exposure of the polymerizable regions to free radicals generated, for example, by photosensitive chemicals and dyes.

An important aspect of the macromers are that the polymerizable regions are separated by at least one degradable region to facilitate uniform degradation in vivo. There are several variations of these polymers. For example, the polymerizable regions can be attached directly to degradable extensions or indirectly via water soluble nondegradable sections so long as the polymerizable regions are separated by a degradable section. For example, if the macromer contains a simple water soluble region coupled to a degradable region, one polymerizable region may be attached to the water soluble region and the other attached to the degradable extension or region. In another embodiment, the water soluble region forms the central core of the macromer and has at least two degradable regions attached to the core. At least two polymerizable regions are attached to the degradable regions so that, upon degradation, the polymerizable regions, particularly in the polymerized gel form, are separated. Conversely, if the central core of the macromer is formed by a degradable region, at least two water soluble regions can be attached to the core and polymerizable regions attached to each water soluble region. The net result will be the same after gel formation and exposure to in vivo degradation conditions. In still another embodiment, the macromer has a water soluble backbone region and a degradable region affixed to the macromer backbone. At least two polymerizable regions are attached to the degradable regions, so that they are separated upon degradation, resulting in gel product dissolution. In a further embodiment, the macromer backbone is formed of a nondegradable backbone having water soluble regions as branches or grafts attached to the degradable backbone. Two or more polymerizable regions are attached to the water soluble branches or grafts. In another variation, the backbone may be star shaped, which may include a water soluble region, a biodegradable region or a water soluble region which is also biodegradable. In this general embodiment, the star region contains either water soluble or biodegradable branches or grafts with polymerizable regions attached thereto. Again, the polymerizable regions must be separated at some point by a degradable region.

Examples of these macromers are PEG-oligoglycolylacrylates. The choice of appropriate end caps permits rapid polymerization and gelation; acrylates were selected because they can be polymerized using several initiating systems, e.g., an eosin dye, by brief exposure to ultraviolet or visible light. The poly(ethyleneglycol) or PEG central structural unit (core) was selected on the basis of its high hydrophilicity and water solubility, accompanied by excellent biocompatibility. A short oligo or poly(α-hydroxy acid), such as polyglycolic acid, was selected as a preferred chain extension because it rapidly degrades by hydrolysis of the ester linkage into glycolic acid, a harmless metabolite. Although highly crystalline polyglycolic acid is insoluble in water and most common organic solvents, the entire macromer is water-soluble and can be rapidly gelled into a biodegradable network while in contact with aqueous tissue fluids. Such networks can be used to entrap and homogeneously disperse water-soluble drugs and enzymes and to deliver them at a controlled rate. Further, they may be used to entrap particulate suspensions of water-insoluble drugs. Other preferred chain extensions are polylactic acid, polycaprolactone, polyorthoesters, and polyanhydrides. Polypeptides may also be used. Such "polymeric" blocks should be understood to include timeric, trimeric, and oligomeric blocks.

These materials are particularly useful for controlled drug delivery, especially of hydrophilic materials, since the water soluble regions of the polymer enable access of water to the materials entrapped within the polymer. Moreover, it is possible to polymerize the macromer containing the material to be entrapped without exposing the material to organic solvents. Release may occur by diffusion of the material from the polymer prior to degradation and/or by diffusion of the material from the polymer as it degrades, depending upon the characteristic pore sizes within the polymer, which is controlled by the molecular weight between crosslinks and the crosslink density. Deactivation of the entrapped material is reduced due to the immobilizing and protective effect of the gel and catastrophic burst effects associated with other controlled-release systems are avoided. When the entrapped material is an enzyme, the enzyme can be exposed to substrate while the enzyme is entrapped, provided the gel proportions are chosen to allow the substrate to permeate the gel. Degradation of the polymer facilitates eventual controlled release of free macromolecules in vivo by gradual hydrolysis of the terminal ester linkages.

An advantage of these macromers are that they can be polymerized rapidly in an aqueous surrounding. Precisely conforming, semi-permeable, biodegradable films or membranes can thus be formed on tissue in situ to serve as biodegradable barriers, as carriers for living cells or other biologically active materials, and as surgical adhesives. In a particularly preferred embodiment, the macromers are applied to tissue having bound thereto an initiator, and polymerized to form ultrathin coatings. This is especially useful in forming coatings on the inside of tissue lumens such as blood vessels where there is a concern regarding restenosis, and in forming tissue barriers during surgery which thereby prevent adhesions from forming.

Examples demonstrate the use of these macromers and polymers for the prevention of postoperative surgical adhesions in rat cecum and rabbit uterine horn models. The polymer shows excellent biocompatibility, as seen by a minimal fibrous overgrowth on implanted samples. Hydrogels for the models were gelled in situ from water-soluble precursors by brief exposure to long wavelength ultraviolet (LWUV) light, resulting in formation of an interpenetrating network of the hydrogel with the protein and glycosaminoglycan components of the tissue. The degradable hydrogel was very effective, both by itself and in combination with tPA, in preventing adhesions.

DESCRIPTION OF THE PREFERRED EMBODIMENTS

Disclosed herein are water soluble, biodegradable polymers formed from macromers containing both water soluble regions as well as biodegradable regions and at least two regions which are polymerizable by free radical initiation, preferably by photopolymerization using visible or long wavelength ultraviolet radiation.

The macromers

In general terms, the macromers are polymers that are soluble in aqueous solutions, or nearly aqueous solutions, such as water with added dimethylsulfoxide. They have three components including a biodegradable region, preferably hydrolyzable under in vivo conditions, a water soluble region, and at least two polymerizable regions. Examples of these structures are shown in FIG. 1.

Figure 1:
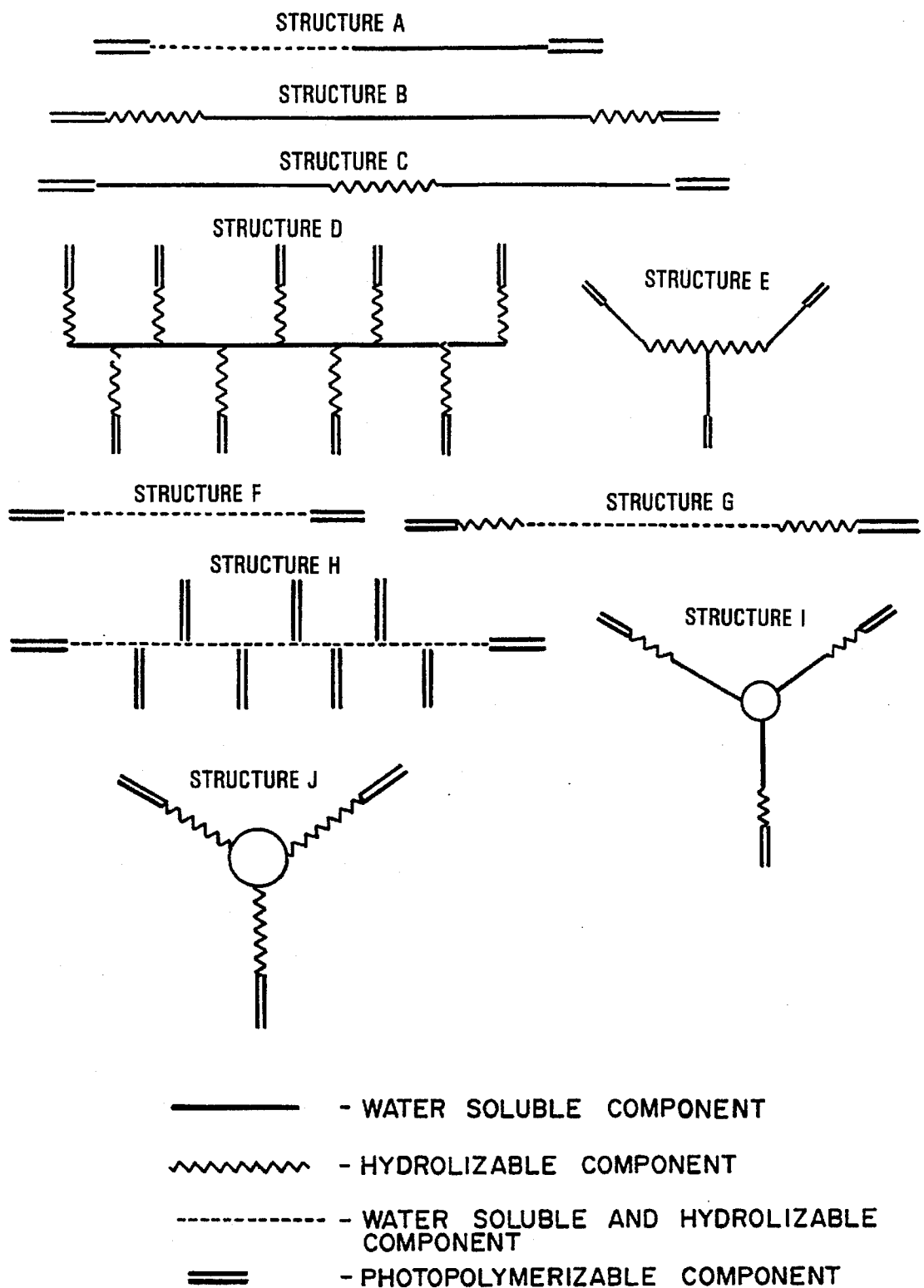
FIG. 1 shows schematically illustrated macromers of the present invention where __ is a water soluble core such as PEG; ~~~~ is a hydrolyzably degradable extension such as a polyglycolide; ===== is a polymerizable end cap or side chain such as an acrylate; and ——— is a water-soluble and hydrolyzable portion such as a hyaluronate.

Structure A in FIG. 1 shows a macromer having a water soluble region (__), a Water soluble and degradable component (———————) appended to one another. Each has a polymerizable end cap (=====). Structure B shows a major water soluble component or core region (__) extended at either end by a degradable or hydrolyzable component (~~~~~) and terminated by, at either end, a polymerizable component (=====). Structure C shows a central degradable or hydrolyzable component (~~~~~) bound to a water soluble component (__) capped at either end by a polymerizable component (=====). Structure D shows a central water soluble component (__) with numerous branches of hydrolyzable components (~~~~~), each hydrolyzable component being capped with a polymerizable component (=====). Structure E shows a central biodegradable, hydrolyzable component (~~~~~) with three water soluble branches (__), each water soluble branch being capped by a polymerizable component (=====). Structure F shows a long central water soluble and hydrolyzable component (————), each end being capped by a polymerizable component (=====). Structure G shows a central water soluble and hydrolyzable component (————) capped at both ends by a hydrolyzable component (~~~~~), each hydrolyzable component being capped by a polymerizable component (=====). Structure H shows a central water soluble and degradable or hydrolyzable component (————) with end caps or branches of a polymerizable component (=====). Structure I shows a central water soluble component (__) in circular form with water soluble branches extended by a hydrolyzable component (~~~~~) capped by a polymerizable component (=====). Lastly, Structure J in FIG. 1 shows a circular water soluble core component (__) with degradable branches (~~~~~), each being capped by a polymerizable component (~~~~~).

The various structures shown in FIG. 1 are exemplary only. Those skilled in the art will understand many other possible combinations which could be utilized for the purposes of the present invention.

Used herein is the term "at least substantially water soluble." This is indicative that the solubility should be at least about 1 g/100 ml of aqueous solution or in aqueous solution containing small amounts of organic solvent, such as dimethylsulfoxide. By the term "polymerizable" is meant that the regions have the capacity to form additional covalent bonds resulting in macromer interlinking, for example, carbon-carbon double bonds of acrylate-type molecules. Such polymerization is characteristically initiated by free-radical formation, for example, resulting from photon absorption of certain dyes and chemical compounds to ultimately produce free-radicals.

In a preferred embodiment, a hydrogel begins with a biodegradable, polymerizable, macromer including a core, an extension on each end of the core, and an end cap on each extension. The core is a hydrophilic polymer or oligomer; each extension is a biodegradable polymer or oligomer; and each end cap is an oligomer, dimer or monomer capable of cross-linking the macromers. In a particularly preferred embodiment, the core includes hydrophilic poly(ethylene glycol) oligomers of molecular weight between about 400 and 30,000 Da; each extension includes biodegradable poly ($\alpha$-hydroxy acid) oligomers of molecular weight between about 200 and 1200 Da; and each end cap includes an acrylate-type monomer or oligomer (i.e., containing carbon-carbon double bonds) of molecular weight between about 50 and 200 Da which are capable of cross-linking and polymerization between copolymers. More specifically, a preferred embodiment incorporates a core consisting of poly (ethylene glycol) oligomers of molecular weight between about 8,000 and 10,000 Da; extensions consisting of poly (lactic acid) oligomers of molecular weight about 250 Da; and end caps consisting acrylate moieties of about 100 Da molecular weight.

Those skilled in the art will recognize that oligomers of the core, extensions and end caps may have uniform compositions or may be combinations of relatively short chains or individual species which confer specifically desired properties on the final hydrogel while retaining the specified overall characteristics of each section of the macromer. The lengths of oligomers referred to herein may vary from two mers to many, the term being used to distinguish subsections or components of the macromer from the complete entity.

Water soluble regions

In preferred embodiments, the core water soluble region can consist of poly(ethylene glycol), poly(ethylene oxide), poly(vinyl alcohol), poly(vinylpyrrolidone), poly (ethyloxazoline), poly(ethylene oxide)-co-poly (propyleneoxide) block copolymers, polysaccharides or carbohydrates such as hyaluronic acid, dextran, heparan sulfate, chondroitin sulfate, heparin, or alginate, proteins such as gelatin, collagen, albumin, ovalbumin, or polyamino acids.

Biodegradable regions

The biodegradable region is preferably hydroiyzable under in vivo conditions. For example, hydrolyzable group may be polymers and oligomers of glycolide, lactide, $\epsilon$-caprolactone, other hydroxy acids, and other biologically degradable polymers that yield materials that are non-toxic or present as normal metabolites in the body. Preferred poly($\alpha$-hydroxy acid)s are poly(glycolic acid), poly(DL-lactic acid) and poly(L-lactic acid). Other useful materials include poly(amino acids), poly(anhydrides), poly (orthoesters), poly(phosphazines) and poly(phosphoesters). Polylactones such as poly($\epsilon$-caprolactone), poly($\epsilon$-caprolactone), poly($\delta$-valerolactone) and poly(gamma-butyrolactone), for example, are also useful. The biodegradable regions may have a degree of polymerization ranging from one up to values that would yield a product that was not substantially water soluble. Thus, monomeric, dimeric, trimeric, oligomeric, and polymeric regions may be used.

Biodegradable regions can be constructed from polymers or monomers using linkages susceptible to biodegradation, such as ester, peptide, anhydride, orthoester, phosphazine and phosphoester bonds.

Polymerizable regions

The polymerizable regions are preferably polymerizable by photoinitiation by free radical generation, most preferably in the visible or long wavelength ultraviolet radiation. The preferred polymerizable regions are acrylates, diacrylates, oligoacrylates, methacrylates, dimethacrylates, oligomethoacrylates, or other biologically acceptable photopolymerizable groups.

Other initiation chemistries may be used besides photoinitiation. These include, for example, water and amine initiation schemes with isocyanate or isothiocyanate containing macromers used as the polymerizable regions.

Photoinitiators and/or Catalysts

Useful photoinitiators are those which can be used to initiate by free radical generation polymerization of the macromers without cytotoxicity and within a short time frame, minutes at most and most preferably seconds. Preferred dyes as initiators of choice for LWUV or visible light initiation are ethyl eosin, 2,2-dimethoxy-2-phenyl acetophenone, other acetophenone derivatives, and camphorquinone. In all cases, crosslinking and polymerization are initiated among macromers by a light-activated free-radical polymerization initiator such as 2,2-dimethoxy-2-phenylacetophenone or a combination of ethyl eosin ($10^{-4}$ to $10^{-2}$M) and triethanol amine (0.001 to 0.1M), for example.

The choice of the photoinitiator is largely dependent on the photopolymerizable regions. For example, when the macromer includes at least one carbon-carbon double bond, light absorption by the dye causes the dye to assume a triplet state, the triplet state subsequently reacting with the amine to form a free radical which initiates polymerization. Preferred dyes for use with these materials include eosin dye and initiators such as 2,2-dimethyl-2-phenylacetophenone, 2-methoxy-2-phenylacetophenone, and camphorquinone. Using such initiators, copolymers may be polymerized in situ by long wavelength ultraviolet light or by laser light of about 514 nm, for example.

Initiation of polymerization is accomplished by irradiation with light at a wavelength of between about 200-700 nm, most preferably in the long wavelength ultraviolet range or visible range, 320 nm or higher, most preferably about 514 nm or 365 nm.

There are several photooxidizable and photoreducible dyes that may be used to initiate polymerization. These include acridine dyes, for example, acriblarine; thiazine dyes, for example, thionine; xanthine dyes, for example, rose bengal; and phenazine dyes, for example, methylene blue. These are used with cocatalysts such as amines, for example, triethanolamine; sulphur compounds, for example, $RSO_2R^1$; heterocycles, for example, imidazole; enolates; organometallics; and other compounds, such as N-phenyl glycine. Other initiators include camphorquinones and acetophenone derivatives.

Thermal polymerization initiator systems may also be used. Such systems that are unstable at 37° C. and would initiate free radical polymerization at physiological temperatures include, for example, potassium persulfate, with or without tetraamethyl ethylenediamine; benzoylperoxide, with or without triethanolamine; and ammonium persulfate with sodium bisulfite.

Applications for the Macromers
Prevention of Surgical Adhesions.

A preferred application is a method of reducing formation of adhesions after a surgical procedure in a patient. The method includes coating damaged tissue surfaces in a patient with an aqueous solution of a light-sensitive free-radical polymerization initiator and a macromer solution as described above. The coated tissue surfaces are exposed to light sufficient to polymerize the macromer. The light-sensitive free-radical polymerization initiator may be a single compound (e.g., 2,2-dimethoxy-2-phenyl acetophenone) or a combination of a dye and a cocatalyst (e.g., ethyl eosin and triethanol amine).

Controlled drug delivery

A second preferred application concerns a method of locally applying a biologically active substance to tissue surfaces of a patient. The method includes the steps of mixing a biologically active substance with an aqueous solution including a light-sensitive free-radical polymerization initiator and a macromer as described above to form a coating mixture. Tissue surfaces are coated with the coating mixture and exposed to light sufficient to polymerize the macromer. The biologically active substance can be any of a variety of materials, including proteins, carbohydrates, nucleic acids, and inorganic and organic biologically active molecules. Specific examples include enzymes, antibiotics, antineoplastic agents, local anesthetics, hormones, antiangiogenic agents, antibodies, neurotransmitters, psychoactive drugs, drugs affecting reproductive organs, and oligonucleotides such as antisense oligonucleotides.

In a variation of the method for controlled drug delivery, the macromers are polymerized with the biologically active materials to form microspheres or nanoparticles containing the biologically active material. The macromer, photoinitiator, and agent to be encapsulated are mixed in an aqueous mixture. Particles of the mixture are formed using standard techniques, for example, by mixing in oil to form an emulsion, forming droplets in oil using a nozzle, or forming droplets in air using a nozzle. The suspension or droplets are irradiated with a light suitable for photopolymerization of the macromer.

Tissue Adhesives

Another use of the polymers is in a method for adhering tissue surfaces in a patient. The macromer is mixed with a photoinitiator or photoinitiator/cocatalyst mixture to form an aqueous mixture and the mixture is applied to a tissue surface to which tissue adhesion is desired. The tissue surface is contacted with the tissue with which adhesion is desired, forming a tissue junction. The tissue junction is then irradiated until the macromers are polymerized.

Tissue Coatings

In a particularly preferred application of these macromers, an ultrathin coating is applied to the surface of a tissue, most preferably the lumen of a tissue such as a blood vessel. One use of such a coating is in the treatment or prevention of restenosis, abrupt reclosure, or vasospasm after vascular intervention. The photoinitiator is applied to the surface of the tissue, allowed to react, adsorb or bond to tissue, the unbound photoinitiator is removed by dilution or rinsing, and the macromer solution is applied and polymerized. As demonstrated below, this method is capable of creating uniform polymeric coating of between one and 500 microns in thickness, most preferably about twenty microns, which does not evoke thrombosis or localized inflammation.

Tissue Supports

The macromers can also be used to create tissue supports by forming shaped articles within the body to serve a mechanical function. Such supports include, for example, sealants for bleeding organs, sealants for bone defects and space-fillers for vascular aneurisms. Further, such supports include strictures to hold organs, vessels or tubes in a particular position for a controlled period of time.

The following examples are presented to describe preferred embodiments and utilities of the present invention and are not meant to limit the invention unless otherwise stated in the claims appended hereto. Taken together, the examples illustrate representative demonstrations of the best mode of implementing the invention as currently understood.

Table 1 shows the code names of the various macromers synthesized in or for use in the examples, along with their composition in terms of the molecular weight of the central PEG segment and the degree of polymerization of the degradable comonomer.

TABLE 1

| Macromer Molecular Weight and Composition. | | | |
|---|---|---|---|
| PEG molecular weight | Comonomer | D.P. of conomoner per OH group | Polymer Code |
| 20,000 | glycolide | 15 | 20 KG |
| 18,500 | glycolide | 2.5 | 18.5 K |
| 10,000 | glycolide | 7 | 10 KG |
| 6,000 | glycolide | 5 | 6 KG |
| 4,000 | glycolide | 5 | 4 KG |
| 1,000 | glycolide | 2 | 1 KG |
| 20,000 | DL-lactide | 10 | 20 KL |
| 18,500 | DL-lactide | 10 | 18.5 KL |

TABLE 1-continued

Macromer Molecular Weight and Composition.

| PEG molecular weight | Comonomer | D.P. of conomoner per OH group | Polymer Code |
|---|---|---|---|
| 10,000 | DL-lactide | 5 | 10 KL |
| 6,000 | DL-lactide | 5 | 6 KL |
| 1,000 | DL-lactide | 2 | 1 KL |
| 600 | DL-lactide | 2 | 0.6 KL |
| 600 | DL-lactide + lactide caprolactone(CL) | 2; CL 1 | 0.6 KLCL |
| 18,500 | caprolactone | 2.5 | 18.5 KCL |
| 18,500 | — | — | 18.5 KCO |

EXAMPLE 1

Synthesis of Photopolymerized Biodegradable Hydrogels

PEG-based hydrogels

PEG-based biodegradable hydrogels are formed by the rapid laser or UV photopolymerization of water soluble macromers. Macromers, in turn, are synthesized by adding glycolic acid oligomers to the end groups of PEG and then capping with acrylic end groups. The PEG portions of the macromers confer water solubility properties, and subsequent polymerization results in cell-nonadhesive hydrogels. Glycolic acid oligomers serve as the hydrolyzable fraction of the polymer network, while acrylic end groups facilitate rapid polymerization and gelation of the macromers.

In preparation for synthesis, glycolide (DuPont) or DL-lactide (Aldrich) was freshly recrystallized from ethyl acetate. PEG oligomers of various molecular weight (Fluka or Polysciences) were dried under vacuum at 110° C. prior to use. Acryloyl chloride (Aldrich) was used as received. All other chemicals were of reagent grade and used without further purification.

Macromer synthesis

A 250 ml round bottom flask was flame dried under repeated cycles of vacuum and dry argon. 20 gm of PEG (molecular weight 10,000), 150 ml of xylene and 10 μgm of stannous octoate were charged into the flask. The flask was heated to 60° C. under argon to dissolve the PEG and cooled to room temperature. 1.16 gm of glycolide was added to the flask and the reaction mixture was refluxed for 16 hr. The copolymer was separated on cooling and was recovered by filtration. This copolymer was separated on cooling and recovered by filtration. This copolymer (10K PEG-glycolide) was used directly for subsequent reactions. Other polymers were similarly synthesized using DL-lactide or ε-caprolactone in place of glycolide and using PEG of different molecular weights.

Synthesis of photosensitive oligomers (macromers):

19 gm of 10K PEG-glycolide copolymer was dissolved in 150 ml methylene chloride and refluxed with 1 ml acryloyl chloride and 1.2 ml of triethylamine for 12 hr under an argon atmosphere. The solid triethylamine hydrochloride was separated by filtration and the polymer was precipitated by adding the filtrate to a large excess of hexane. The polymer (capped by an acrylate at both ends) was further purified by repeated dissolution and precipitation in methylene chloride and hexane respectively.

Table 2 lists certain macromers synthesized. The degree of polymerization of the glycolide chain extender was kept low so that all polymers have approximately 10 ester groups per chain, or about 5 per chain end. When these polymers are photopolymerized, a crosslinked three-dimensional network is obtained. However, each chain segment in the resulting network needs just one ester bond cleaved at either end to "degrade." These ester cleavages enable the chain to dissolve in the surrounding physiological fluid and thereby be removed from the implant site. The resulting hydrolysis products, PEG and glycolic acid, are water soluble and have very low toxicity.

TABLE 2

| | Macromers Synthesized | | | | |
|---|---|---|---|---|---|
| Polymer Code | Mol. Wt. of Central PEG Chain (daltons) | % Glycolide in Extremeties | % ε-Caprolactone in Extremities | Calculated Mol. Wt. of Extremities (daltons) | Appearance |
| 0.4 K | 400 | 100 | — | 580 | Viscous liquid |
| 1 KG | 1000 | 100 | — | 300 | Viscous liquid |
| 4 KG | 4000 | 100 | — | 232 | White solid |
| 10 KG | 10000 | 100 | — | 580 | White solid |
| 18.5 KG | 18500 | 100 | — | 1160 | Yellow solid |
| col 8.5 KGCL | 18500 | 50 | — | 580 | White solid |

Due to the presence of only a few units of glycolic acid per oligomeric chain, the solubility properties of the photo-crosslinkable prepolymers are principally determined by the central PEG chain. Solubility of the macromers in water and methylene chloride, both of which are solvents for PEG, is not adversely affected as long as the central PEG segment has a molecular weight of 1,000 daltons or more. Solubility data for the prepolymers synthesized is given in Table 3.

TABLE 3

| | SOLUBILITY DATA | | | | |
|---|---|---|---|---|---|
| Solvent | 1 KG | 4 KG | 10 KG | 18.5 KG | TMP* |
| DMSO | — | ■ | — | ■ | ■ |
| Acetone | — | ■ | ■ | ■ | — |
| Methanol | — | ■ | — | ■ | — |
| Water | — | — | — | — | ■ |
| Hexane | ■ | ■ | ■ | ■ | ■ |
| Methylene Chloride | — | — | — | — | — |
| Cold Xylene | ■ | ■ | ■ | ■ | — |
| Hot Xylene | — | — | — | — | — |
| Benzene | ■ | ■ | ■ | ■ | — |

— Soluble
■ Not Soluble
*Trimethylolpropane glycolide triacrylate

PEG chains with different degrees of polymerization of DL-lactide were synthesized to determine the degree of substitution for which water solubility of the macromers can be retained. The results are shown in Table 4. Beyond about 20% substitution of the hydrophilic PEG chain with hydrophobic DL-lactoyl or acrylate terminals leads to the macromers becoming insoluble in water, though they are still soluble in organic solvents such as methylene chloride.

TABLE 4

| | Solubility of Macromers | | |
|---|---|---|---|
| D.P.* of Ethylene Oxide | D.P.* of lactide or glycolide | % extension of PEG chain | Solubility in water |
| 420 | 4 | 0.1 | soluble |
| 420 | 10 | 2.4 | soluble |
| 420 | 20 | 4.8 | soluble |
| 420 | 40 | 9.5 | soluble |
| 420 | 80 | 19 | insoluble |
| 23 | 2 | 8.7 | soluble |
| 23 | 4 | 17.4 | soluble |
| 23 | 10 | 43.5 | insoluble |
| 23 | 40 | 174 | insoluble |
| 5 | 4 | 80 | insoluble |
| 10 | 4 | 40 | soluble |

*degree of polymerization

Photopolymerization

The macromers can be gelled by photopolymerization using free radical initiators, with the presence of two acrylic double bonds per chain leading to rapid gelation. A 23% w/w solution of various degradable polymers in HEPES buffered saline containing 3 μl of initiator solution (300 mg/ml of 2,2-dimethoxy-2-phenyl-acetophenone in n-vinyl pyrrolidone) was used. 100 μl of the solution was placed on a glass coverslip and irradiated with a low intensity long wavelength UV (LWUV) lamp (Blak-Ray, model 3–100A with flood). The times required for gelation to occur were noted and are given below. These times are typically in the range of 10 seconds. This is very significant because these reactions are carried out in air (UV initiated photopolymerizations are slow in air as compared to an inert atmosphere) and using a portable, low powered long wave UV (LWUV) emitting source. Oxygen, which often inhibits free radical reactions by forming species which inhibit propagation, did not seem to slow down the polymerization. Such fast polymerizations are particularly useful in applications requiring in situ gelations. This rapid gelation is believed to be due to the formation of micelle-like structures between the relatively hydrophobic polymerizable groups on the macromer, thereby increasing the local concentration of the polymerizable species in aqueous solution and increasing polymerization rates.

Visible laser light is also useful for polymerization. Low intensity and short exposure times make visible laser light virtually harmless to living cells since the radiation is not strongly absorbed in the absence of the proper chromophore. Laser light can also be transported using fiber optics and can be focused to a very small area. Such light can be used for rapid polymerization in highly localized regions; gelation times for selected prepolymers are given in Table 5. In each case, 0.2 ml of a 23% w/v photosensitive oligomer solution is mixed with ethyl eosin ($10^{-4}$M) and triethanol amine (0.01 to 0.1M) and the solution is irradiated with an argon ion laser (American argon ion laser model 905 emitting at 514 nm) at a power of 0.2–0.5 W/cm$^2$. The beam is expanded to a diameter of 3 mm and the sample is slowly scanned until gelation occurs.

TABLE 5

| | Gelation Times | |
|---|---|---|
| Polymer | UV polymerization* gelation time (mean ± S.D.) (s) | Laser Polymerization** gelation time (s) |
| 1 KG | 5.3 ± 4.1 | <1 |
| 4 KG | 14.7 ± 0.5 | <1 |
| 6 KG | 9.3 ± 0.5 | <1 |
| 10 KG | 18. ± 0.8 | <1 |
| 10 KL | 7.7 ± 0.5 | <1 |
| 18 KG | 23.3 ± 1.2 | <1 |
| 20 KG | 13.3 ± 0.5 | <1 |

*Initiator: 2,2-dimethoxy-2-phenylacetophenone, concentration 900 ppm: 0.2 ml of 23% monomer solution in PBS
**Argon ion laser emitting at 514 nm. power 3 W/cm$^2$: ethyloeosin, triethanol amine initiating system: 0.2 ml of 23% monomer solution in PBS Biodegradability Biodegradation of the resulting polymer network is an important criteria in many biomedical applications. Degradation of poly(glycolic acid) and poly(DL-lactic acid) has been well documented in the literature. The degradation mainly takes place through the hydrolysis of the ester bond; the reaction is second order and highly pH dependent. The rate constant at pH 10 is 7 times faster than that at pH 7.2.

Such facile biodegradation is surprising because poly(α-hydroxyacidesters) are hydrophobic and highly insoluble in water. Accessibility of the polymer matrix to the aqueous surrounding is therefore limited. However, because the networks are hydrogels which are swollen with water, all the ester linkages in the network are in constant contact with water with the aqueous surroundings. This results in a uniform bulk degradation rather than a surface degradation of these gels.

Table 6 gives hydrolysis data for some of these networks; times listed are for complete dissolution of 60 mg of gel at pH 7.2 and 9.6. As noted, most of the gels dissolve within 12 hours at pH 9.6. 18.5 k gel dissolves within 2.5 hr at pH 9.6 whereas 18.5KCO gel does not dissolve in 3 days, indicating that the lactoyl, glycoloyl, or ε-caprolactoyl ester moiety is responsible for degradation of these networks. It also can be seen that the 18.5KG gel hydrolyzes more rapidly than the 4KG gel. This may be due to the reduced hydrophilicity and higher crosslink density of the latter gel.

TABLE 6

| | Hydrolysis Data | |
|---|---|---|
| Oligomer used for gelation | Time taken to dissolve gel at pH 9.6 (h) | Time taken to dissolve gel at pH 7.2 (days) |
| 4 KG | 6.2 | 5.5 |
| 10 KG | 12.25 | 5.5 |
| 18.5 KG | 2.25 | >7 |
| 18.5 KCL | >5 days | >7 |
| 18.5 KCO | >5 days | >7 |

Characterization of macromers

FTIR spectra of the prepolymers were recorded on a DIGILAB model FTS 15/90. The absorption at 1110 cm$^{-1}$ (characteristic C-0-C absorption of PEG) shows the presence of PEG segments. The strong 1760 cm$^{-1}$ absorption shows the presence of glycolic ester. The absence of hydroxyl group absorption around 3400 cm$^{-1}$ and a weak acrylic double bond absorption at 1590 cm$^{-1}$ shows the presence of acrylic double bonds at the end groups.

500 MHz proton and 125 MHz carbon-13 spectra were recorded on a GE 500 instrument. The presence of a very strong peak at 4.9 ppm due to $CH_2$ methylene from the PEG segment, a peak at 5.09 ppm due to the glycolic ester segment and an acrylic proton singlet at 5.8 ppm can be easily seen from proton NMR. The estimated molecular weight of PEG segment and glycolic acid segment for different copolymers is shown in Table 2. The carbonyl peak at 169.39 ppm from glycolic acid and 36.5 ppm peak from methylene carbons from PEG in carbon-13 NMR are consistent with the reported chemical composition of these copolymers.

Differential scanning calorimetry (Perkin Elmer DSC-7) was used to characterize the oligomers for thermal transitions. The oligomers were heated from 40° C. to 200° C. at a rate of 20° C./min, presumably causing polymerization. The polymer was then cooled to −40° C. at a rate of 60° C./min and again heated to 200° C. at a rate of 20° C./min. The first scans of biodegradable 18.5K PEG glycolide tetraacrylate (18.5KG) oligomer were compared to that of the non-degradable 18.5K PEG tetraacrylate (18.5KCO) scan. It was seen that a glass transition appears in the 18.5KG at −2° C. while no such transition exists in the 18.5KCO. A small melting peak at 140° C. was also evident due to the few glycolic acid mers which can crystallize to a limited extent. The melting peak for PEG is shifted downwards in 18.5KG to 57° C. from 60.7° C. for 18.5KCO. This is probably due to disturbance of the PEO crystalline structure due to the presence of the glycolic acid linkages. In the third cycle, by which time the oligomers have presumably polymerized, the Tg and Tm transitions for the glycolide segments can no longer be seen, indicating that a crosslinked network has formed and the glycolic acid segments are no longer capable of mobility.

Figure 1A:
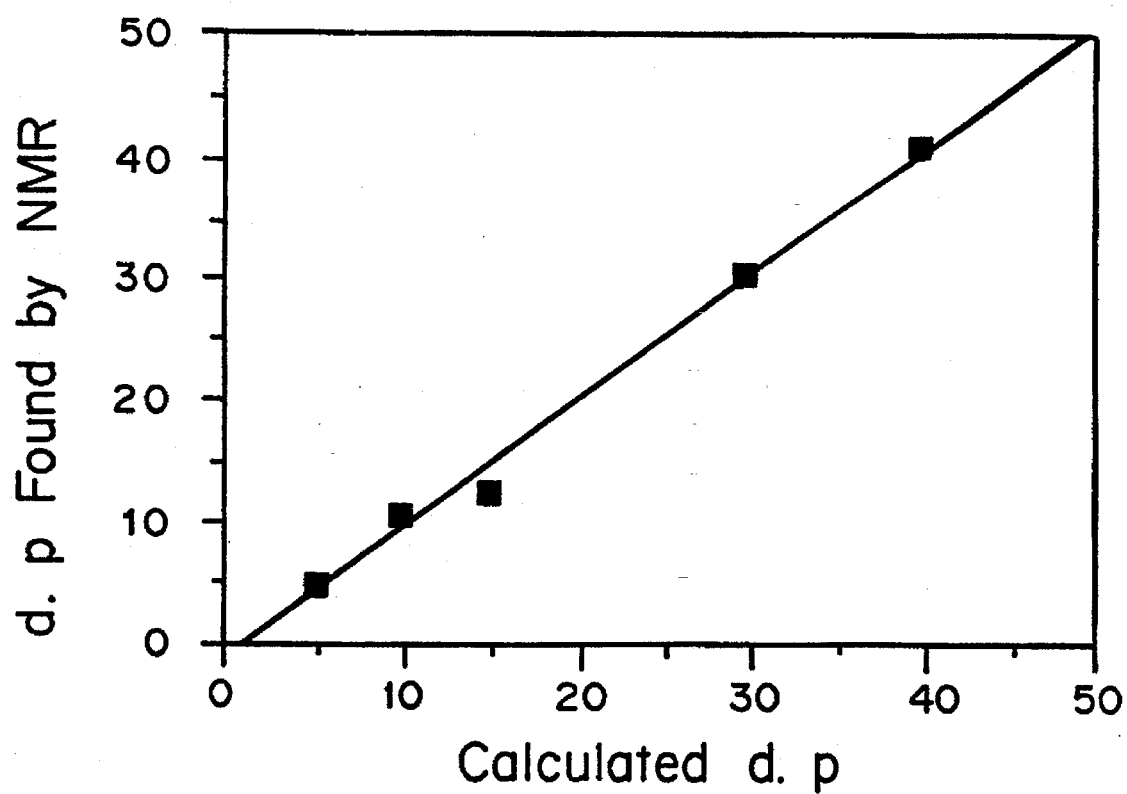
FIG. 1A shows the degree of photopolymerization (dp) calculated and found by NMR.

The degree of polymerization (D.P.) of the degradable segments added to the central water soluble PEG chain was determined in several cases using $^1$H NMR. The experimentally determined D.P. was seen to be in good agreement with the calculated number, as shown by FIG. 1A. Thus, the ring opening reaction initiated by the PEG hydroxyls proceeds to completion, giving quantitative yields.

Determination of Total Water, Free Water Bound Water

Solutions of various degradable macromers were made as described above. Gels in the shape of discs were made using a mold. 400 µl of solution was used for each disc. The solutions were irradiated for 2 minutes to ensure thorough gelation. The disc shaped gels were removed and dried under vacuum at 60° C. for 2 days. The discs were weighed (W1) and then extracted repeatedly with chloroform for 1 day. The discs were dried again and weighed (W2). The gel fraction was calculated as W2/W1. This data appears in Table 7.

Subsequent to extraction, the discs were allowed to equilibrate with PBS for 6 hours and weighed (W3 after excess water had been carefully swabbed away). The total water content was calculated as (W3-W2) X 100/W3. Differential scanning calorimetry (DSC) was used to determine the amount of free water that was available in the gels. A scan rate of 20° C./min was used and the heat capacity for the endotherm for water melting was measured (H1). The heat capacity of HBS was also measured (H2). The fraction of free water was calculated as H1/H2. The residual water was assumed to be bound due to hydrogen bonding with the PEO segments. The presence of free water in the gels was indicated. This free water can be expected to help proteins and enzymes entrapped in such gels in maintaining their native conformation and reducing deactivation. Thus these gels would appear to be suited for controlled release of biological micromolecules. The data for gel water content is summarized in Table 7

TABLE 7

| Polymer Code | Hydrogel Water content | | | |
| --- | --- | --- | --- | --- |
| | % Free Water | % Bound Water | % Total Water | % Gel Content |
| 1 KG | 68.4 | 14 | 82.3 ± 2.6 | 61.3 ± 5.2 |
| 4 KG | 78.0 | 9.3 | 87.3 ± 1.8 | 56.3 ± 0.9 |
| 6 KG | 74.8 | 13.4 | 88.1 ± 3.3 | 66.5 ± 2.35 |
| 10 KG | 83.7 | 10.8 | 94.5 ± 0.5 | 54.3 ± 0.6 |
| 10 KL | 82.0 | 9.7 | 91.7 ± 0.5 | 63.9 ± 3.7 |
| 18.5 KG | 71.8 | 22.3 | 94.0 ± 0.4 | 47.0 ± 4.9 |
| 20 KG | 79.8 | 14.8 | 94.5 ± 0.4 | 44.5 ± 4.8 |

EXAMPLE 2

Use of multifunctional macromers 30 g of a tetrafunctional water soluble PEG (MW 18,500) (PEG 18.5 k) was dried by dissolving the polymer in benzene and distilling off the water benzene azeotrope. In a glove bag, 20 g of PEG 18.5 k, 1.881 g of glycolide and 15 mg of stannous octoate were charged into a 100 ml round bottom flask. The flask was capped with a vacuum stopcock, placed into a silicone oil bath and connected to a vacuum line. The temperature of the bath was raised to 200° C. The reaction was carried out for 4 hours at 200° C. and 2 hours at 160° C. The reaction mixture was cooled, dissolved in dichloromethane and the copolymer was precipitated by pouring into an excess of dry ethyl ether. It was redissolved in 200 ml of dichloromethane in a 500 ml round bottom flask cooled to 0° C. To this flask, 0.854 g of triethylamine and 0.514 ml of acryloyl chloride were added under nitrogen atmosphere and the reaction mixture was stirred for 12 h. at 0° C. The triethyl amine hydrochloride was separated by filtration and the copolymer was recovered from filtrate by precipitating in diethyl ether. The polymer was dried at 50° C. under vacuum for 1 day.

EXAMPLE 3

Synthesis of a photosensitive macromer containing DL-lactide

PEG (MW) 20,000) (PEG 20k) was dried by dissolving in benzene and distilling off the water benzene azeotrope. In a glove bag, 32.43 g of PEG 20k, 2.335 g of DL-lactide and 15 mg of stannous octoate were charged into a 100 ml round bottom flask. The flask was capped with a vacuum stopcock, placed into a silicone oil bath and connected to a vacuum line. The temperature of the bath was raised to 200° C. The reaction was carried out for 4 hours at 200° C. The reaction mixture was cooled, dissolved in dichloromethane and the copolymer was precipitated by pouring into an excess of dry ethyl ether. It was redissolved in 200 ml of dichloromethane in a 500 ml round bottom flask cooled to 0° C. To this flask, 0.854 g of triethylamine and 0.514 ml of acryloyl chloride were added under nitrogen atmosphere and the reaction mixture was stirred for 12 hours at 0° C. The triethyl amine hydrochloride was separated by filtration and the copolymer was recovered from filtrate by precipitating in diethyl ether. The polymer was dried at 50° C. under vacuum for 1 day.

EXAMPLE 4

Synthesis of a Photosensitive Precursor Containing DL-Lactide and ε-Caprolactone.

PEG (MW 600) (PEG 0.6k) was dried by dissolving in benzene and distilling off the water benzene azeotrope. In a glove bag, 0.973 g of PEG 0.6 k, 0.467 g of DL-lactide along with 0.185 g of ε-caprolactone and 15 mg of stannous octoate were charged into a 50 ml round bottom flask. The flask was capped with a vacuum stopcock, placed into a silicone oil bath and connected to a vacuum line. The temperature of the bath was raised to 200° C. The reaction was carried out for 4 hours at 200° C. and 2 hours at 160° C. The reaction mixture was cooled, dissolved in dichloromethane and the copolymer was precipitated by pouring into an excess of dry ethyl ether. It was redissolved in 50 ml of dichloromethane in a 250 ml round bottom flask cooled to 0° C. to this flask, 0.854 g of triethylamine and 0.514 ml of acryloyl chloride were added under nitrogen atmosphere and the reaction mixture was stirred for 12 hours at 0° C. The triethyl amine hydrochloride was separated by filtration and the copolymer was recovered from filtrate by precipitating in diethyl ether. The polymer was dried at 50° C. under vacuum for 1 day and was a liquid at room temperature.

EXAMPLE 5

Selection of dyes for use in photopolymerization

It is possible to initiate photopolymerization with a wide variety of dyes as initiators and a number of electron donors as effective cocatalysts. Table 8 illustrates photopolymerization initiated by several other dyes which have chromophores absorbing at widely different wavelengths. All gelations were carried out using a 23% w/w solution of 18.5KG in HEPES buffered saline. These initiating systems compare favorably with conventional thermal initiating systems, as can also be seen from Table 8. Other photoinitiators that may be particularly useful are 2-methoxy-2-phenyl acetophenone and camphorquinone.

TABLE 8

| Polymerization Initiation of 18.5 KG PEG | | | |
|---|---|---|---|
| INITIATOR | LIGHT SOURCE* | TEMPERATURE °C. | GEL TIME (SEC) |
| Eosin Y, 0.00015M; Triethanolamine 0.65M | S1 with UV filter | 25 | 10 |
| Eosin Y, 0.00015M; Triethanolamine 0.65M | S4 | 25 | 0.1 |
| Methylene Blue, 0.00024M; p-toluenesulfinic acid, 0.0048M | S3 | 25 | 120 |
| 2,2-dimethoxy-2-phenyl acetophenone 900 ppm | S2 | 25 | 8 |
| Potassium persulfate 0.0168M | — | 75 | 180 |
| Potassium Persulfate 0.0168M; tetramethyl ethylene-diamine 0.039M | — | 25 | 120 |
| Tetramethyl ethylene-diamine 0.039M; Riboflavin 0.00047M | S1 with UV filter | 25 | 300 |

*LIST OF LIGHT SOURCES USED
CODE  SOURCE

S1  Mercury lamp, LEITZ WETSLER Type 307-148.002, 100 W
S2  Black Ray longwave UV lamp, model B-100A W/FLOOD
S3  MELLES GRIOT He—Ne laser, 10 mW output, 1 = 632 nm
S4  American laser corporation, argon ion laser, model 909BP-15-01001; λ = 488 and 514 nm Numerous other dyes can be used for photopolymerization. These dyes include but are not limited to: Erythrosin, phloxine, rose bengal, thioneine, camphorquinone, ethyl eosin, eosin, methylene blue, and riboflavin. The several possible cocatalysts that can be used include but are not limited to: N-methyl diethanolamine, N,N-dimethyl benzylamine, trierhanoi amine, triethylamine, dibenzyl amine, N-benzyl ethanolamine, N-isopropyl benzylamine, and N-vinyl pyrrolidinone.

EXAMPLE 6

Thermosensitive Biodegradable Gels from N-Isopropyl Acrylamide

Synthesis of low molecular weight polyisopropyl acrylamide

N-isopropyl acrylamide (NIPAAm) was recrystallized from 65:35 hexane benzene mixture. Azobisisobutyronitrile (AIBN) was recrystallized from methanol. 1.5 g of NIPAAm was polymerized using 3 mg of AIBN and 150 mg of mercaptoethanol in 1:1 acetone water mixture (24 hours at 65° C.). The viscous liquid after polymerization was purified by dissolving in acetone and precipitating in diethyl ether. Yield 80%.

This hydroxy terminated low molecular weight poly (NIPAAm) was used in chain extension reactions using glycolide and subsequent endcapping reaction using acryloyl chloride as described in other examples.

1 g of modified poly(NIPAAm) based oligomer and 0.2 g 1KL were dissolved in water at 0° C. and polymerized at 0° C. using 2-2-dimethoxy-2-phenylacetophenone (900 PPM).

EXAMPLE 7

In Vitro Degradation

The gels were extracted as described in Example 1 to remove the unpolymerized macromer fraction fraction and the gels were then placed in 50 mM HEPES buffered saline (0.9% NaCl), pH 7.4 at 37° C. Duplicate samples were periodically removed, washed with fresh HBS and dried at 100° C. for 1 day and weighed to determine mass loss in the gel. The compositions of the various gels used were the same as described in the previous examples. Table 9 shows the extent of degradation of these gels given as percent of mass lost over time. The respective times are given in parenthesis along with the mass loss data.

TABLE 9

| Gel Degradation | |
|---|---|
| 1 KG | 20.1% (1 d), 20.36 ± 0.6 (2d), 21.7± (6d), 28.8 ± 16.6 (10 d) estimated total Degradation time 45 days. |
| 4 KG | 38.9 (1d), 60.3 ± 4.2 (2d), 78.9 (3d), 99.3 ± 4.7 (6d). Total degradation time 5.5 days. |
| 6 KG | 18.3 ± 6.8 (1d), 27.4 ± 1.0 (2d), 32.8 ± 11.3 (3d), 104.8 ± 3.2 (5d). total degradation time 4.5 days 10 KG 0.6 ± 0.6 (8 hr), 100 (1d). Total degradation time 1 day. |
| 10 KL | 10.0 ± 4.84 (2d), 6.8 ± 1.7 (3d), 4.5 ± 3.1 (6d), 8.0 ± 0.2 (10d). Total degradation time estimated to be 20 days. |
| 20 KG | 68.1 ± 4.2 (8 hr), 99.7 ± 0.3 (1d). Total degradation time 15 hr. |

EXAMPLE 8

Fibroblast adhesion and spreading

The in vitro response of Human foreskin fibroblast (HFF) cells to photopolymerized gels was evaluated through cell culture on polymer networks. 0.2 ml of monomer solution was UV polymerized on an 18×18 mm glass coverslips under sterile conditions. HFF cells were seeded on these gels at a cell density of $1.8 \times 10^4$ cells/sq cm of coverslip area in Dulbecco's Modified Eagle's Medium (DMEM) supplemented with 10% fetal calf serum. The gels were incubated for 6 hr at 37° C. in a 5% $CO_2$ environment, at the end of which they were washed twice with phosphate buffered saline (PBS). The adherent cells were fixed using a 2% glutaraldehyde solution in PBS. The gels were examined under a phase contrast microscope at a magnification of 200X, and the number of adherent and spread cells evaluated by examining five fields selected at predetermined locations on the coverslips.

The number of adherent cells is reported in Table 10 along with those for glass control surfaces. Cell adhesion is seen to be dramatically lowered on gel-coated glass.

TABLE 10

| Cell Adhesion | |
| --- | --- |
| Surface | Attached Cells/cm$^2$ |
| glass | 13220 ± 3730 |
| 18.5 KG | 250 ± 240 |
| 18.5 KCL | 1170 ± 1020 |
| 18.5 KCO | 390 ± 150 |

Figure 2A:
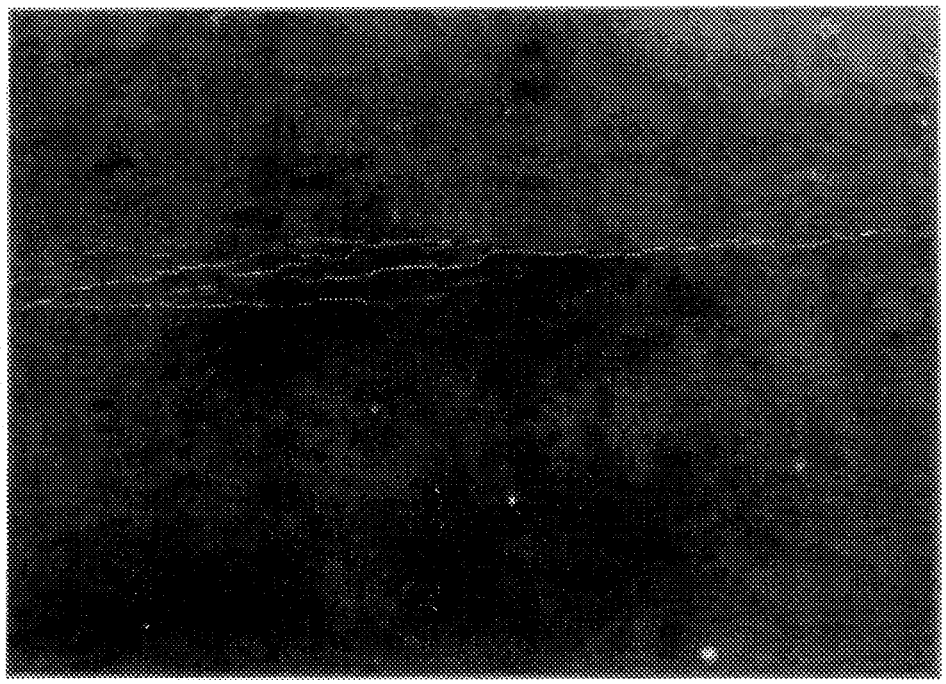
FIG. 2A shows Human foreskin fibroblasts cultured for six hours on glass coverslips coated with PEG 18.5K-glycolide diacrylate (18.5KG).
Figure 2B:
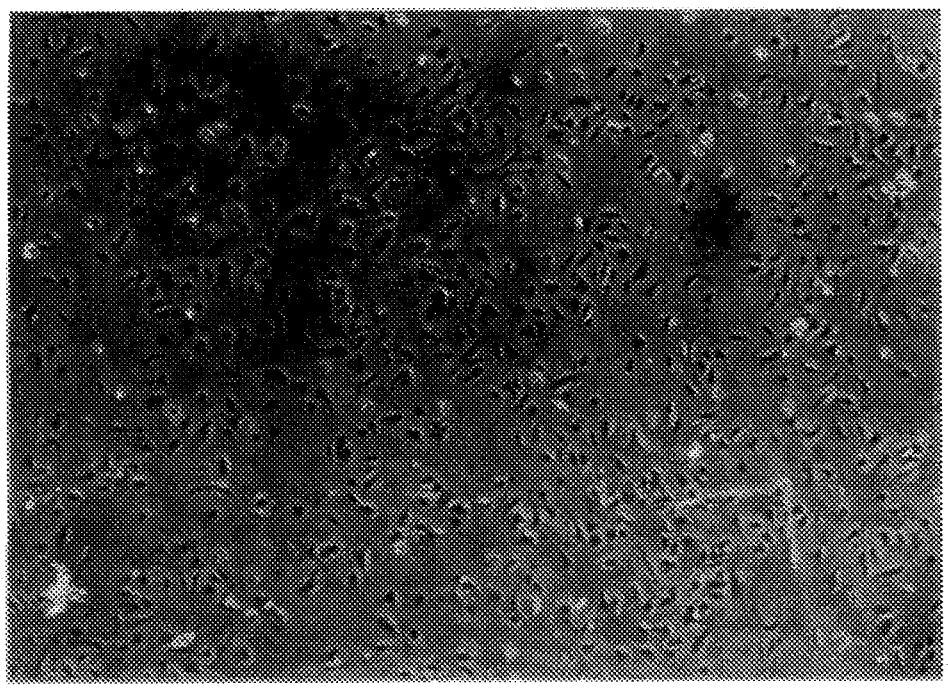
FIG. 2B shows Human foreskin fibroblasts cultured for six hours on glass coverslips not coated with PEG.

Typical photographs of these cells on the 18.5KCL gel surfaces and on control glass surfaces are shown in FIGS. 2A and 2B. It can be easily seen from Table 10 that these gels are highly resistant to cellular growth. Even the 18.5KCL is still less than 10% of the glass. Cells attached to the glass surface show a flattened and well-spread morphology whereas the few cells that are attached to the gel are rounded and loosely attached. This may result from the fact that hydrated PEG chains have a high motility and have been shown to be effective in minimizing protein adsorption. One of the mechanisms by which cell adhesion is mediated is through the interaction of cell surface receptors with adsorbed cell adhesion proteins. Thus the reduction in overall protein adsorption results in minimal cell adhesion protein adsorption and reduced cell adhesion.

EXAMPLE 9

Release of Protein (Bovine Serum Albumin) from Polymers

Figure 3A:
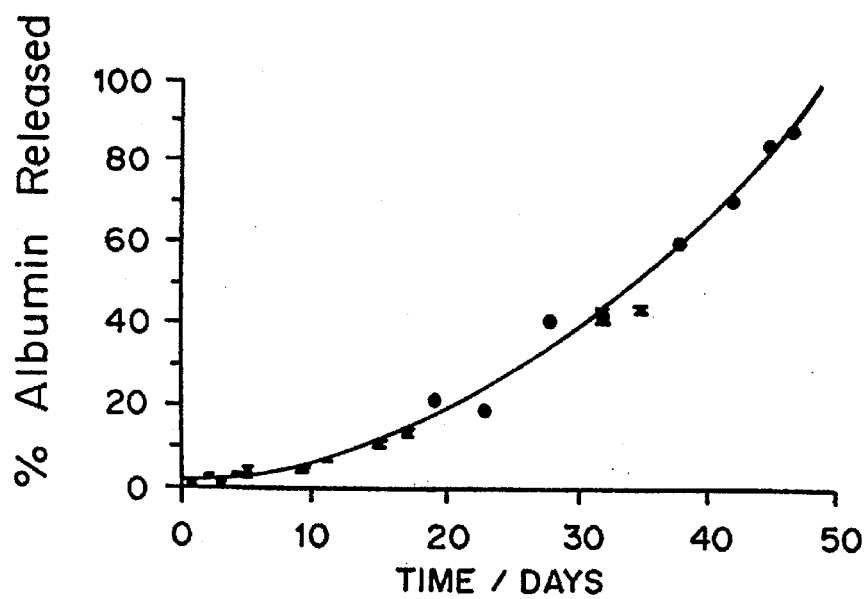
FIG. 3A shows the release of BSA from a PEG 1K (1000 molecular weight PEG) glycolide diacrylate with glycolide extensions (1 KG) hydrogel into PBS.

1KG was used for this study. This macromer was liquid at room temperature and was used as such. 1 mg of bovine serum albumin (BSA) was added per ml of monomer solution along with 0.9 mg/ml of 2,2-dimethoxy-2-phenyl-acetophenone as initiator. The protein was dissolved in the monomer solution and disc shaped gels were made by exposing 0.2 g of macromer mixture to LWUV for 1 min. Two such discs were placed in a flask containing 20 ml of PBS and incubated at 37° C. Two aliquots of 20 µl each were removed from these flasks periodically and the amount of BSA released was assayed using the Bio-Rad total protein assay. The release profile for BSA is shown in FIG. 3A. It can be seen that the release of BSA is relatively steady over more than a month.

EXAMPLE 10

Enzyme Release Assay

Water solubility of the macromers means gelation can be carried out in a non-toxic environment. This makes these materials suitable for intraoperative uses where in situ gelation is needed. Since the precursors are water soluble, the gels can be used as drug delivery vehicles for water soluble drugs, especially macromolecular drugs such as enzymes, which would otherwise be denatured and lose their activity. Release of lysosome and tPA from the polymers was used to illustrate the feasibility of using biodegradable hydrogels for controlled release of biomolecules.

Lysozyme release

Figure 3B:
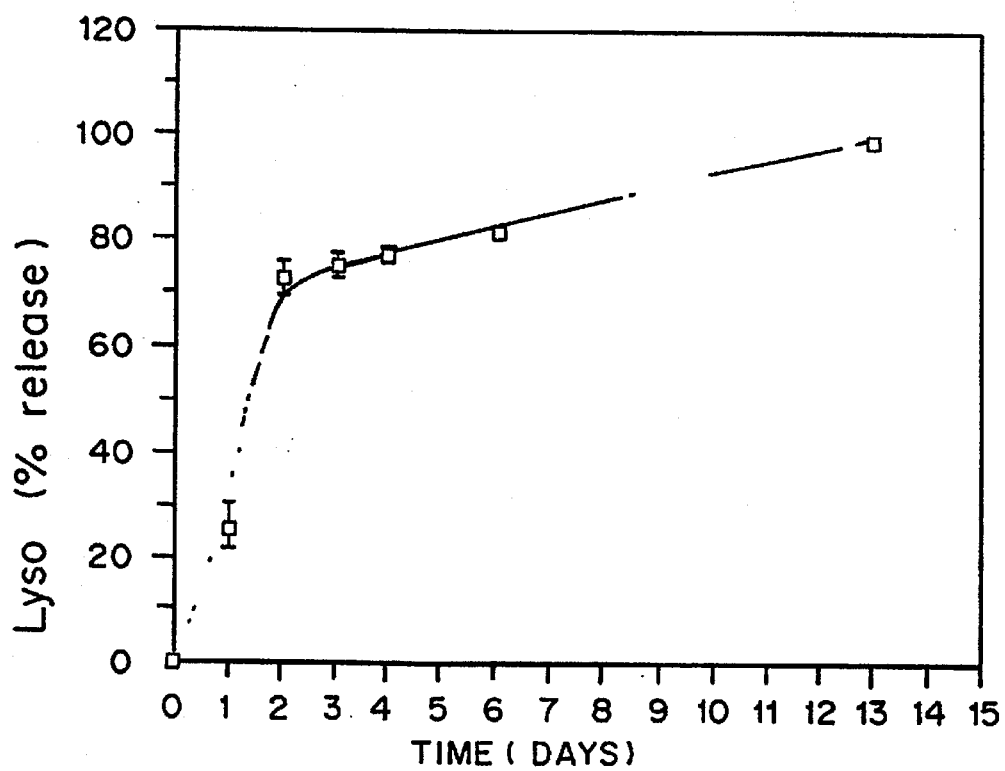
FIG. 3B shows release of lysozyme from PEG 18.5K-DL-lactide tretraacrylate (18.5KL) into PBS.

The enzyme lysozyme (MW:14,400) is a convenient model for release of a low molecular weight protein from a biodegradable gel. The Biorad total protein assay was used to quantify the enzyme released. The enzyme was dissolved in PBS at a concentration of 20 mg/ml. The monomer PEG-dl-lactic acid-diacrylate was dissolved in PBS to produce a 40% solution. The lysozyme solution was added to the monomer solution to attain a 24% monomer solution. The monomer/lysozyme solution was polymerized under UV in a cylindrical mold, using 30 µl of the initiator 2,2-dimethoxy-2-phenyl-acetophenone in 1-vinyl-2-pyrrolidone (30 mg/ml) as the initiator. The polymer was cut into 10 equal sized pieces and immersed in 10 ml PBS. Samples of the PBS were withdrawn at intervals and assayed for lysozyme released into the PBS. Lysozyme was released from the PEG-DL-lactic acid-diacrylate gel over an 8 day interval, with the maximum rate of release occurring within the first 2 days, as shown by FIG. 3B.

Release of recombinant t-PA

Figure 4A:
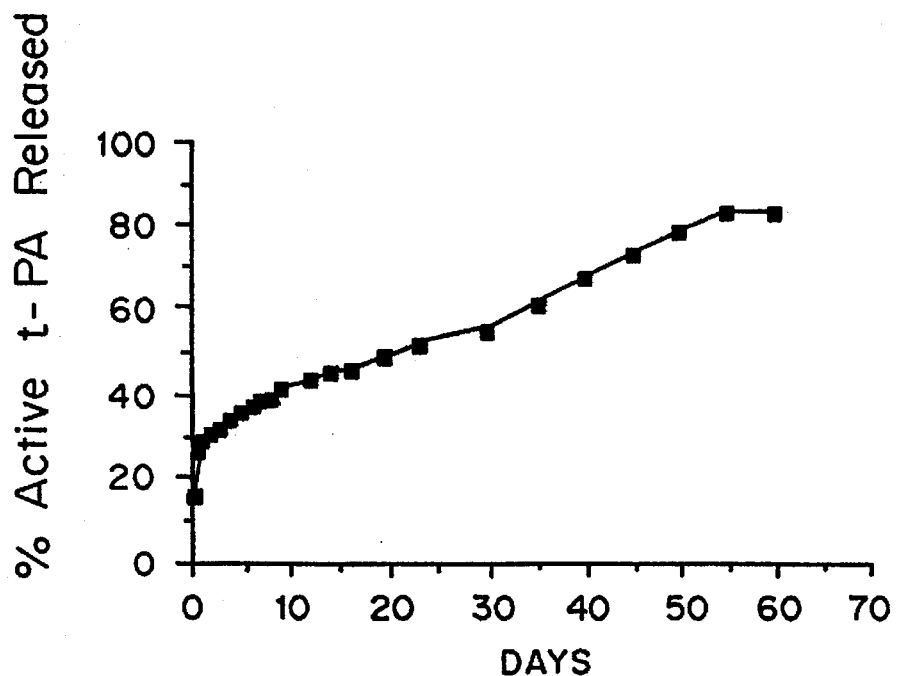
FIG. 4A shows release of active recombinant t-PA from a PEG 1K lactide diacrylate (1KL) hydrogel.
Figure 4B:
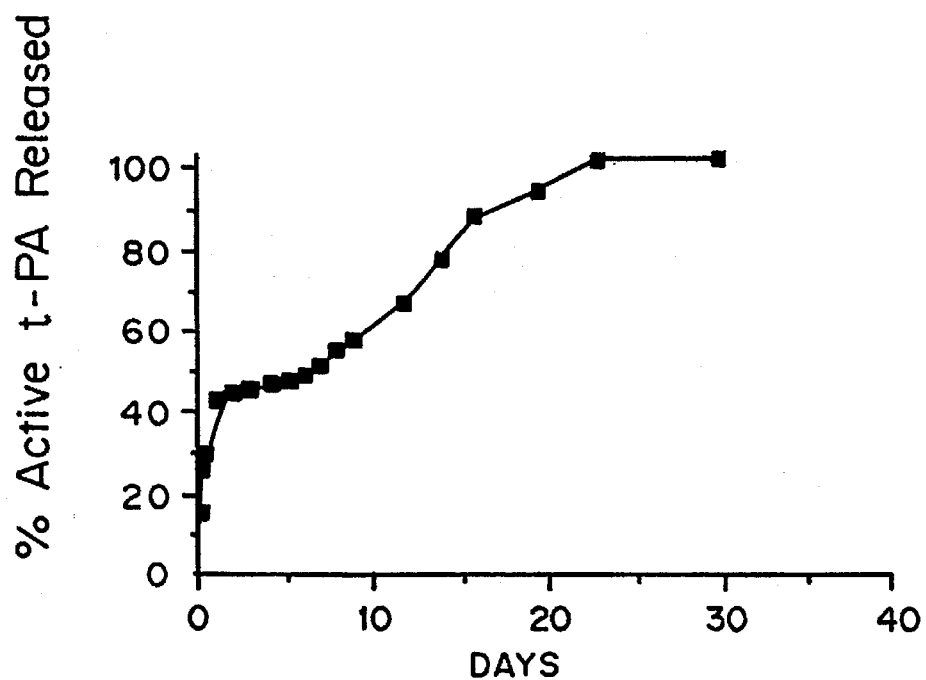
FIG. 4B shows release of active recombinant t-PA from PEG 4K glycolide diacrylate (4KG) hydrogel.
Figure 4C:
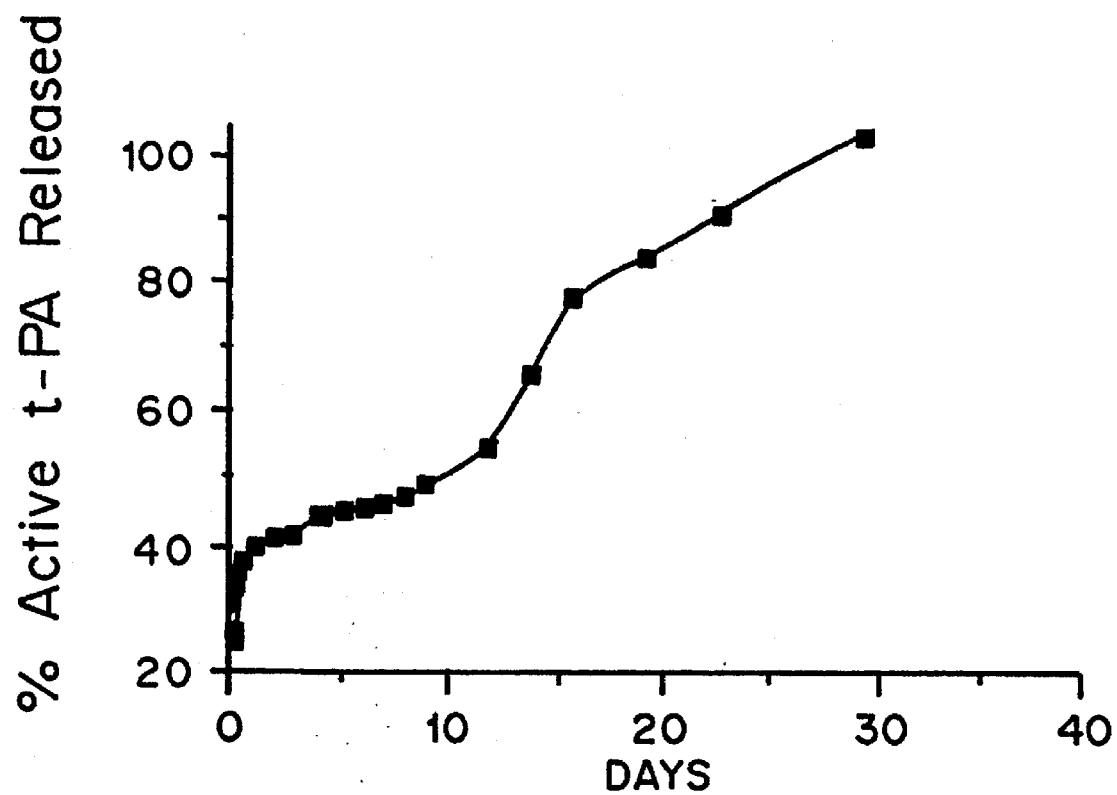
FIG. 4C shows release of active recombinant t-PA from a PEG 18.5K-glycolide diacrylate (18.5KG) hydrogel into PBS.

Three macromers were used for these studies: 1KL, 4KG, and 18.5KG. The 1KL macromer was liquid at room temperature and was used as such. The second macromer, 4KG, was used as a 75% w/w solution in PBS. The third composition was a mixture of equal parts of 1KL and a 50% w/w solution of 18.5KG. 3.37 mg of tissue plasminogen activator (single chain, recombinant, M.W. 71,000) was added per gram of macromer solution along with 0.9 mg/ml of 2,2 dimethoxy 2 phenyl acetophenone as initiator. The protein was dissolved with the macromer and disc shaped gels were made by exposing 0.2 g of macromer mixture to LWUV for 1 minute. Two such discs were rinsed with PBS, placed in a flask containing 5 ml of PBS and incubated at 37° C. Two aliquots of 100 µl each were removed from these flasks periodically and the amount of active t-PA released was assayed using a chromogenic substrate assay (Kabi-vitrum). The release profiles from the 1K lactide gels, 4K glycolide gels, and the 50/50 1K glycolide/18.5K glycolide are shown in FIGS. 4A–4C. Fully active tPA can be released for periods up to at least two months.

By selecting an appropriate formulation, the release rate can be tailored for a particular application. It is also possible to combine formulations with different molecular weights so as to synergistically achieve appropriate attributes in release and mechanical characteristics.

For prevention of postoperative adhesions, in addition to the barrier effect of the gels, the gels can be loaded with a fibrinolytic agent to lyse incipient filmy adhesions which escape the barrier effect. This further enhances the efficacy of biodegradable gels in adhesion prevention.

EXAMPLE 11

Toxicity of Polymers and Commercial Adhesives

To evaluate the toxicity of in situ polymerization of the macromer solutions described herein, as compared to commercial adhesives, 100 µl of 18.5KCO prepolymer solution was placed on the right lobe of a rat liver and gelled by exposing it to LWUV for 15 sec; similarly, a few drops of a n-butyl cyanoacrylate based glue were placed on the left lobe. The liver was excised after a week, fixed in 10% neutral buffered formalin, blocked in paraffin, sectioned and stained using hematoxylin and eosin.

No adverse tissue reaction was evident on the surface of the lobe exposed to the biodegradable gel. No inflammatory reaction to the polymerization process can be seen. The epithelium looks normal, with no foreign body reaction.

In comparison, the lobe exposed to cyanoacrylate glue shows extensive tissue necrosis and scarring with 10–30 cell deep necrotic tissue. Fibrosis is evident in the necrotic portions close to underlying normal tissue.

EXAMPLE 12

Prevention of Post-Surgical Adhesions with Photopolymerized Biodegradable Polymer A viscous sterile 23% solution in phosphate buffered saline (8.0 g/l NaCl, 0.201 g/l KCl, 0.611 g/l $Na_2HPO_4$, 0.191 g/l $KH_2PO_4$, pH 7.4) of polyethylene glycol (M.W. 18,500) which has been chain extended on both ends with a short polyglycolide repeat unit (average number of glycolidyl residues: 10 on each end) and which has been subsequently terminated with an acrylate group was prepared. Initiator needed for the crosslinking reaction, 2,2-dimethoxy-2-phenyl acetophenone, was added to the macromer solution to achieve an initiator concentration of 900 ppm. A 30 second exposure to a long wave UV lamp (Blak Ray) is sufficient to cause polymerization.

Animal models evaluated

Animal models evaluated included a rat cecum model and a rabbit uterine horm model. In the rat cecum mode, 6 out of 7 animals treated with the macromer solution showed no adhesions whatsoever, while untreated animals showed consistent dense adhesion formation. In the rabbit uterine horn model, a significant (p<0.01) reduction in adhesion formation was seen in the animals treated with the gel. Studies conducted in rats using only the ungelled viscous precursor solution (no LWUV) failed to prevent the formation of adhesions.

Rat cecum model

Twenty-one Sprague Dawley male rats having an average weight of 250 gm were divided into three groups for treatment and two for controls. The abdomen was shaved and prepared with a betadine solution. A midline incision was made under Equithesin anesthesia. The cecum was located and 4 to 5 scrapes were made on a region about 2×1 cm on one side of the cecum, using a 4×4 in gauze pad to produce serosal injury and punctate bleeding. The abdominal incisions in these animals were closed using a continuous 4–0 silk suture for the musculoperitoneal layer and 7.5 mm stainless steel staples for the cutaneous layer. A topical antibiotic was applied at the incision site.

The first group consisted of 7 animals serving as controls without treatment, to confirm the validity of the model. The second group served as a control with the application of the precursor but without photopolymerization to form the hydrogel. After induction of the cecal injury, about 0.25 ml of the precursor solution was applied to the injury site using a pipet. The abdominal incision was then closed as above.

The third group served as the gel treatment group and was prepared as the second group except that the precursor film was exposed to a LWUV lamp for 45 seconds to cause gelation. Both the obverse and reverse sides of the cecum were similarly treated with precursor and light. No attempt was made to dry the surface of the tissue, to remove blood, or to irrigate the area prior to treatment.

The animals were sacrificed at the end of two weeks by $CO_2$ asphyxiation. The incisions were reopened and adhesions were scored for location, extent, and tenacity. The extent of adhesions was reported as a percentage of the traumatized area of the cecum which forms adhesions with adnexal organs or the peritoneal wall. Tenacity of the adhesions was scored on a scale from 0 to 4: no adhesions—grade 0; tentative transparent adhesions which frequently separate on their own—grade 1; adhesions that give some resistance but can be separated by hand—grade 2; adhesions that require blunt instrument dissection to separate—grade 3; and dense thick adhesions which require sharp instrument dissection in the plane of the adhesion to separate—grade 4.

Rat cecum model results

The control group without treatment shows consistently dense and extensive adhesions. The extent of abraded area covered with adhesions was seen to be 73±21% (mean±S.D., n=7). The severity of adhesions was grade 3.5±0.4. Most of the adhesions were dense and fibrous, involving the cecum with itself, with the peritoneal wall and with other organs such as the liver, small intestine, and large intestine. Frequently the nesentery was seen to be involved in adhesions. In the control group with the application of precursor solution but without gelation by exposure to the LWUV lamp, the extent of adhesion was 60±24% (n=7), and the severity of adhesions was 3.1±0.4. In the gel treated group, the cecum was seen to be completely free of adhesions in 6 out of 7 animals. In one case, a grade 2 adhesion was seen with the mesentery over 10% of the area and a grade 2.5 adhesion was seen over 15% of the area, bridging the cecum to the sutures on the site of the incision in the peritoneal wall. The overall adhesion extent for the group was 4%, and the overall severity was 0.32. No evidence of residual gel was visible, the gel presumably having degraded within the prior two weeks. The cecum appeared whitish with a fibrous layer on the surface in the control group, but the tissue appeared healthy and normal in animals treated with the gel.

Rabbit uterine horn model

Eight sexually mature female New Zealand rabbits between 2 and 3 kg in weight were prepared for surgery. A midline incision was made in the lower abdominal region under Rompun, Ketamine, and Acepromazine anesthesia. The uterine horns were located and the vasculature to both horns was systematically cauterized to induce an ischemic injury. One animal was rejected from the study due to immature uterine horns. Seven rabbits were selected for the treatment with only the photopolymerizable hydrogel and two animals were selected for evaluating the combined efficacy of the hydrogel with a fibrinolytic agent, tissue plasminogen activator (tPA). 5 mg of tPA/ml macromer solution was used in the latter case. After cauterization, macromer solutions (0.5 ml) were applied along the horn and allowed to coat the surface where the cauterization injury had been induced. After uniform application of the solution was complete, the horns were exposed to a LWUV lamp for 1 min to induce gelation. The procedure was repeated on the reverse side of the horns. The incisions were then closed using a continuous 2-0 Vicryl (Ethicon) suture for the musculoperitoneal layer and a 0 Vicryl (Ethicon) suture for the cutaneous layer. No prophylactic antibiotics were administered. No postoperative complications or infections were observed. Five animals were used in the control group. The ischemic injury was made as described and the incision was closed without the application of the precursor; all techniques were identical between the treatment group and the control group.

Controls were used where the same animal model was subjected to surgery without application of the macromer; all surgical techniques were identical between the treatment group and the historical controls.

The rabbits were reoperated under Ketamine anesthesia at the end of two weeks to evaluate adhesion formation; they were sacrificed by introcardiac KCl injection. Adhesion formation was evaluated for extent and tenacity. Extent of adhesion formation was evaluated by measuring the length of the uterine horn that formed adhesions with itself or with the peritoneal wall or other organs. Tenacity of adhesion was classified as either filmy or fibrous. Filmy adhesions were usually transparent, less strong, and could be freed by hand. The fibrous adhesions were dense, whitish, and usually required sharp instrument dissection to be freed. In cases where only a single filmy adhesion band was evident, a score of 5% was assigned.

Typical samples of the horn were excised for histology and were fixed in a 10% neutral buffered formalin solution. Paraffin sections of the samples were stained using hematoxylin and eosin.

Rabbit uterine horn model results

Figure 5A:
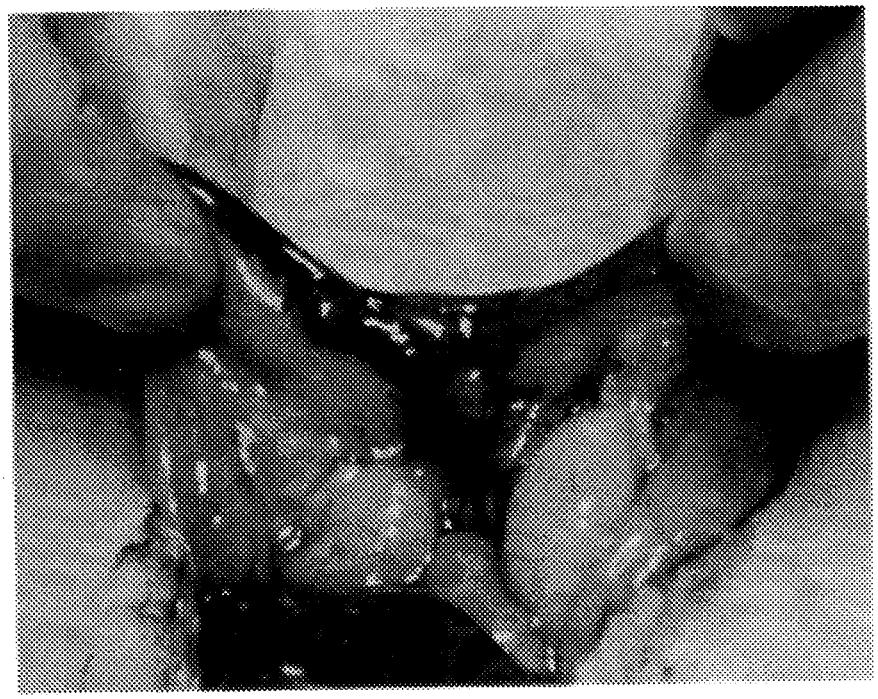
FIG. 5A is a superior view of rabbit uterine horn used as a control. Distorted horn anatomy with 66% adhesions is evident. The horns are folded upon themselves.

The adhesion score is the % of affected area occupied by the adhesions, with grading of each as being filmy or fibrous. Distorted horn anatomies were observed in control animals. The mean score in the control group was 50±15% of the affected area of the horn being occupied by adhesions with 10% of these being filmy and 90% fibrous. Distorted horn anatomies were observed, as can be seen from FIG. 5A which presents a superior view of the uterine horn in an animal used as a control, which showed adhesions over 66% of the horn surface. The group of animals treated only with the photopolymerized macromer showed an adhesion score of 13±11.4% (n=10). Of these, 4 animals showed less than 5% adhesions with only an occasional filmy band visible.

The animals treated with photopolymerized gel containing tPA showed further improved results over the "gel only" animals. One animals showed a filmy band on both the right and left horn. They were assigned a score of 5% with a total score of 10%. The other animal did not show any adhesions at all. Thus the total score for these animals was 5±5%.

Figure 5B:
FIG. 5B is a superior view of rabbit uterine horn treated with a photopolymerized biodegradable hydrogel, PEG 18.5KL. Horn anatomy is normal, with no adhesion bands visible.

FIG. 5B shows normal horn anatomy in a typical horn which has undergone gel treatment. Adhesions are filmy in all cases and no dense bands are seen. No traces of the remaining gel could be observed. Typical samples of horns showing filmy adhesions showed some fibrous tissue with a 6–15 cell thick layer of fibroblasts showing some collagen fibrils but no formation of dense collagen fibers. The horns showing no adhesions occasionally showed a 1–4 cell thick layer of fibroblasts, but mostly a normal epithelium with no evidence of inflammatory cells.

This same procedure was slightly modified as described below as a better mode of using the polymers to prevent postoperative adhesions using the rat uterine horn model.

Female rats were anesthetized with pentobarbital (50 mg/kg, intraperitoneally), and a midline laparotomy was performed. The uterine horns were exposed, and the vasculature in the arcade feeding the horns was systematically cauterized using bipolar cautery; the most proximal and most distal large vessel on each horn were not cauterized. Following this, the antimesenteric surface of each horn was cauterized at two 1 mm diameter spots on each horn, each separated by a 2 cm distance, the pair centered along the length of each horn. Following injury, 0.5 ml of macromer solution was applied per horn and was gelled by exposure to long wavelength ultraviolet light (365 nm, approximately 20 mW/cm$^2$) for 15 sec per surface on the front side and on the back side each. The uterus was replaced in the peritoneal cavity, and the musculoperitoneal and skin layers were closed.

The macromer consisted of a PEG chain of MW 8,000 daltons, extended on both sides with a lactic acid oligomer of an average degree of polymerization of 5 lactidyl groups, and further acrylated nominally at both ends by reaction with acryloyl chloride. In one batch, Batch A, the degree of acrylation was determined by NMR to be approximately 75%, and in another, Batch B, it was determined to be greater than approximately 95%. The macromer was dissolved in saline at a specified concentration, and the initiation system used was 2,2-dimethoxy-2-phenyl acetophenone from a stock solution in N-vinyl pyrrolidinone, the final concentration of 2,2-dimethoxy-2-phenyl acetophenone being 900 ppm and the final concentration of N-vinyl pyrrolidinone being 0.15%.

In one set of experiments, macromet from Batch A was applied in varying concentrations, and adhesions were scored at 7 days postoperatively. Scoring was performed by two means. The length of the horns involved in adhesions was measured with a ruler, and the fraction of the total length was calculated. The nature of the adhesions was also scored on a subjective scale, 0 being no adhesions, 1 being filmy adhesions that are easily separated by hand, and 2 being dense adhesions that can only be separated by sharp instrument dissection. Furthermore, one of the samples contained tissue-plasminogen activator (t-PA), which is known to reduce adhesions, at a concentration of 0.5 mg/ml (0.5%) macromer solution. The results are shown in Table 11 for macromer batch A and batch B.

In a third set of experiments, adhesions were formed in female rats as described above, and the adhesions were surgically lysed 7 days after the initial surgery. The extent and grade of adhesions was scored during lysis. The animals were divided into two groups, and one group was treated with macromer from Batch B at a concentration of 10%. The results are shown in Table 11 as batch B, 10%.

TABLE 11

| | Reduction of Adhesions with Polymer. | | |
|---|---|---|---|
| Concentration macromer | Extent of adhesions % (S.D.) | Grade of adhesions (0–2) | Number of Animals |
| Polymer A | | | |
| 15% | 24.6 (3.1) | 1.1 (0.1) | 7 |
| 20% | 33.6 (9.8) | 1.2 (0.3) | 7 |
| 25% | 37.5 (11.1) | 1.2 (0.1) | 7 |
| 30% | 54.2 (12.0) | 1.6 (0.4) | 6 |
| 20% + t-PA | 18.3 (6.4) | 1.1 (0.1) | 6 |
| Control (saline) | 72.6 (18.7) | 1.5 (0.2) | 7 |
| Polymer B | | | |
| 5% | 22.1 (4.2) | 1.2 (0.1) | 7 |
| 10% | 10.0 (5.1) | 1.0 (0) | 7 |
| 15% | 17.8 (5.7) | 1.0 (0) | 7 |
| 20% | 26.3 (11.4) | 1.4 (0.2) | 7 |
| Control (saline) | 75.9 (4.4) | 1.8 (0.3) | 7 |
| Polymer B, 10% | | | |

Scoring      group
performed    that

TABLE 11-continued

Reduction of Adhesions with Polymer.

| Concentration macromer | | Extent of adhesions % (S.D.) | Grade of adhesions (0–2) | Number of Animals |
|---|---|---|---|---|
| at: | became: | | | |
| time of lysis | Controls | 85.9 (9.7) | 1.8 (0.1) | 7 |
| Time of lysis | Treatment | 79.4 (6.8) | 1.7 (0.2) | 7 |
| 7 days post-lysis | Controls | 78.8 (11.3) | 1.8 (0.1) | 7 |
| 7 days post-lysis | Treatment | 28.2 (5.1) | 1.0 (0) | 7 |

The above results illustrate that the photopolymerized macromer can reduce or prevent post operative adhesions in both primary adhesions and adhesiolysis models, and moreover that the gel can be used to locally release a drug to exert a combined beneficial effect.

EXAMPLE 13

Nerve anastomosis

The sciatic nerve of a rat was aseptically severed using a scalpel and allowed to pull apart. The two ends of the nerve were reopposed using sterile forceps, and a 50% solution in buffer of polymer 1KL, a macromer made from PEG 1K with lactide chain extension and acrylate termination, with 0.1% 2,2-dimethoxy-2-phenoxy acetophenone was applied to the nerve stumps. The affected area was illuminated with a 100 W LWUV lamp for 60 seconds, and an adhesive bond was observed to form between the proximal and distal nerve stumps.

To ensure the biocompatibility of the applied material with the nerve tissue, the same solution of macromer was applied to nonsevered rat sciatic nerves, and the area of the incision was closed using standard small animal surgical technique. The area was reopened at 1 hour or 24 hour postoperatively, and the affected area of the nerve was removed en block and prepared for transmission electron microscopy. No morphological differences were observable between the treated nerves at either time point as compared to control rat sciatic nerves that were otherwise nonmanipulated, even though they had been traumatized and manipulated.

EXAMPLE 14

Evaluation of PEG Based Degradable Gels as Tissue Adhesives

Abdominal muscle flaps from female New Zealand white rabbits were excised and cut into strips 1 cm×5 cm. The flaps were approximately 0.5 to 0.8 cm thick. A lap joint, 1 cm×1 cm, was made using two such flaps. Two different compositions, 0.6KL and 1 KL, were evaluated on these tissues. Both these compositions were viscous liquids and were used without further dilution. 125 µl of ethyl eosin solution in N-vinyl pyrrolidone (20 mg/ml) along with 50 µl of triethanolamine was added to each ml of the adhesive solution. 100 µl of adhesive solution was applied to each of the overlapping flaps. The lap joint was then irradiated by scanning with a 2 W argon ion laser for 30 sec from each side. The strength of the resulting joints was evaluated by measuring the force required to shear the lap joint. One end of the lap joint was clamped and an increasing load was applied to the other end, while holding the joint was clamped and an increasing load was applied to the other end, while holding the joint horizontally until it failed. Four joints were tested for each composition. The 1KL joints had a strength of 6.6±1.0 KPa (mean ±S.D.), while the 0.6KL joints had a strength of 11.4±2.9KPa. It is significant to note that it was possible to achieve photopolymerization and reasonable joint strength despite the 6–8 mm thickness of tissue. A spectrophotometric estimate using 514 nm light showed less than 1% transmission through such muscle tissue.

EXAMPLE 15

Coupling of Photopolymerizable Groups to Proteins (Albumin)

PEG (M.W. 2,000) monoacrylate (5 g) was dissolved in 20 ml dichloromethane. Triethyl amine (0.523 g) and 2,2, 2-trifluoroethanesulfonyl chloride (tresyl chloride) (0.017 g) were added and the reaction was allowed to proceed for 3 hours at 0° C. under nitrogen atmosphere. The reaction mixture was then filtered and the dichloromethane evaporated to dryness. The residue was redissolved in a small amount of dichloromethane and precipitated in diethyl ether. The polymer was then filtered and dried under vacuum for 10 hours and used directly in the subsequent reaction with albumin.

1 g of bovine serum albumin was dissolved in 200 ml of sodium bicarbonate buffer at pH 9. Tresyl activated PEG monoacrylate (5 g) was added and the reaction was stirred for 24 hours at 25° C. Albumin was separated by pouring the reaction mixture into acetone. It was further purified by dialysis using a 15,000 daltons cutoff dialysis membrane. A 10% w/v solution of the PEG acrylated albumin could be photopolymerized with long wave UV radiation using 0.9 mg/ml of 2,2 dimethoxy 2 phenylacetophenone as the initiator. In this gel the degradable segment is the protein albumin.

EXAMPLE 16

Modification of Polysaccharides (Hyaluronic Acid)

In a dry 250 ml round bottom flask, 10 grams of PEG 400 monomethacrylate was dissolved in 100 ml dry dioxane, to which 4.053 g of carbonyl diimidazole (CDI) was slowly introduced under nitrogen atmosphere and the flask was heated to 50° C. for 6 h. Thereafter the solvent was evaporated under vacuum and the CDI activated PEG monomer was purified by dissolving in dichloromethane and precipitating in ether twice.

1 g of hyaluronic acid, 5 g of CDI activated PEG 400 monoacrylate were dissolved in 200 ml sodium borate buffer (pH 8.5) and the solution was stirred for 24 hours. It was then dialyzed using a 15,000 dalton cutoff dialysis membrane to remove unreacted PEG. A 10% w/v solution of the acrylated hyaluronic acid was photopolymerized with long wave UV radiation, using 0.9 mg/ml of 2,2-dimethoxy-2-phenylacetophenone as the initiator. In this gel, the degradable region is hyaluronic acid.

EXAMPLE 17

PEG Chain Extended with Polyorthocarbonates and Capped with Urethane Methacrylate 3, 9-bis(methylene) 2,4,8,10-tetraoxaspiro [5,5]undecane (1 g) and polyethylene glycol (molecular weight, 1,000, 7.059 g) were weighed into a 250 ml Schlenk tube under dry nitrogen atmosphere in a glove bag. 50 ml of dry tetrahydrofuran was introduced under nitrogen atmosphere and reaction mixture was stirred for 6 hours at 50° C. This is a typical step growth reaction with a disturbed stoichiometry, resulting in low molecular weight poloyorthocarbonate with terminal hydroxy groups. The oligomer was separated by precipitating in hexane and dried under vacuum. 5 g of oligomer was redissolved in dry THF to which 20 µl of dibutyltindilaurate and 2 ml of 2-isocyanatoethyl methacrylate were slowly introduced and temperature was raised to 50° C. It was held there for 6 hours and cooled. The product was separated by precipitation in hexane. In this gel, the degradable region is a polyorthocarbonate.

EXAMPLE 18

Microencapsulation of Animal Cells

A 23% w/w solution of 18.5KG in HEPES buffered saline (5 ml) was used to resuspend $10^6$ CEM-SS cells. Ethyl eosin ($10^{-4}$ M) was used as a solution in N-vinyl pyrrolidone as the initiator and triethanolamine (0.01M) was used as the coinitiator. The solution was then exposed through a coextrusion apparatus to an argon ion laser (514 nm, 2 Watts). The coextrusion apparatus had mineral oil as the fluid flowing annularly (flow rate 4 ml/min) around an extruding stream of the precursor cell suspension (flow rate 0.5 ml/min). The microdriplets gelled rapidly on being exposed to the laser light and were collected in a container containing PBS. The oil separated from the aqueous phase and the microspheres could be collected in the PBS below. The microspheres formed were thoroughly washed with PBS buffer to remove unreacted monomer and residual initiator. The size and shape of microspheres was dependent on extrusion rate and extruding capillary diameter (18 Ga to 25 Ga). The polymerization times were dependent on initiator concentration (ethyl eosin 5 µM to 0.5 mM, vinyl pyrrolidone (0.001% to 0.1%), and triethanolamine (5 mM to 0.1M), laser power (120 mW to 2W), and monomer concentration (>10%w/v). Spheres prepared using this method had a diameter from 500 µm to 1,200 µm. The polymerizations were carried out at physiological pH in the presence of air. This is significant since radical polymerizations may be affected by the presence of oxygen. Cell viability subsequent to encapsulation was checked by trypan blue exclusion assay and the encapsulated cells were found to be more than 95% viable after encapsulation.

EXAMPLE 19

Various Formulations for the Prevention of Post Operative Adhesions

The utility of PEG-oligo(α-hydroxy acid) diacrylates and tetraacrylates to prevent postoperative adhesions was evaluated in the rabbit uterine horn model as described above. The following polymers were synthesized, as described above: PEG 6K lactide diacrylate (6KL), PEG 10K lactide diacrylate (10KL), PEG 18.5K lactide (18.5KL), PEG 20K lactide (20KL). Solutions with 24% polymer in PBS with 900 ppm 2,2-dimethoxy-2-phenyl acetophenone, were prepared as described above. The solutions were applied to the uterine horn after cautery of the vascular arcade and illuminated with a 365 nm LWUV lamp, as described above. In one formulation, 18.5KL, 5 mg t-PA was mixed into the solution before application. Controls consisted of animals manipulated and cauterized but not treated with macromer solution. Measurement was performed on the 14th±1 day. Extent of adhesion was estimated from the fraction of the horn that was involved in adhesions, and the tenacity of adhesions was scored as 0, no adhesions; 1, filmy adhesions that offer no resistance to dissection; 2, fibrous adhesions that are dissectable by hand; 3, fibrous adhesions that are dissectable by blunt instruments; and 4, fibrous adhesions that are dissectable by sharp instruments. The results were as follows, where the extent of adhesions and the tenacity of the adhesions are shown.

TABLE 12

Efficacy of Polymer in Preventing Adhesions.

| Formulation | Number of animals | Extent, %, ± S.D. | Tenacity, 0–4 ± S.D. |
|---|---|---|---|
| 6 KL | 7 | 0.9 ± 1.7 | 0.9 ± 0.7 |
| 10 KL | 7 | 0 ± 0 | 0 ± 0 |
| 20 KL | 6 | 4.4 ± 5.0 | 0.9 ± 0.7 |
| 18.5 KL t-PA | 7 | 8.9 ± 13.1 | 1.6 ± 1.3 |
| Control | 7 | 35 ± 22 | 3.3 ± 0.6 |

EXAMPLE 20

Polymerization of Ultrathin layers of Polymer on the surface of blood vessels to reduce thrombosis after vessel injury Blood vessels were harvested from rats and were rinsed free of blood. The endothelium of the vessel were removed by inserting a wooden dowel and rotating the vessel over the dowel. One vessel was used as a control, and was exposed to flowing blood as described below without further modification. Another vessel was treated first by exposure to eosin Y at 1 mM in saline, then rinsed in HEPES buffered saline, then filled with a solution of PEG-MA, PEG 10K with acrylate end-capped oligomers of DL lactide, containing triethanolamine (TEA) (100 mM) and N-vinylpyrrolidone (VP) (0.15%) and then illuminated by exposure to an argon ion laser at 0.5 W/cm² for 15 sec. The nonpolymerized prepolymer mixture in the lumen of the vessel was rinsed away with saline. Human blood was collected from the antecubital vein and was anticoagulated with heparin at 2 units/ml. This blood was perfused through each vessel by a syringe pump at a flow rate corresponding to a wall shear rate of approximately 200/s for 7 min. The vessel was then superficially rinsed in saline and fixed in formaldehyde.

Figure 6A:
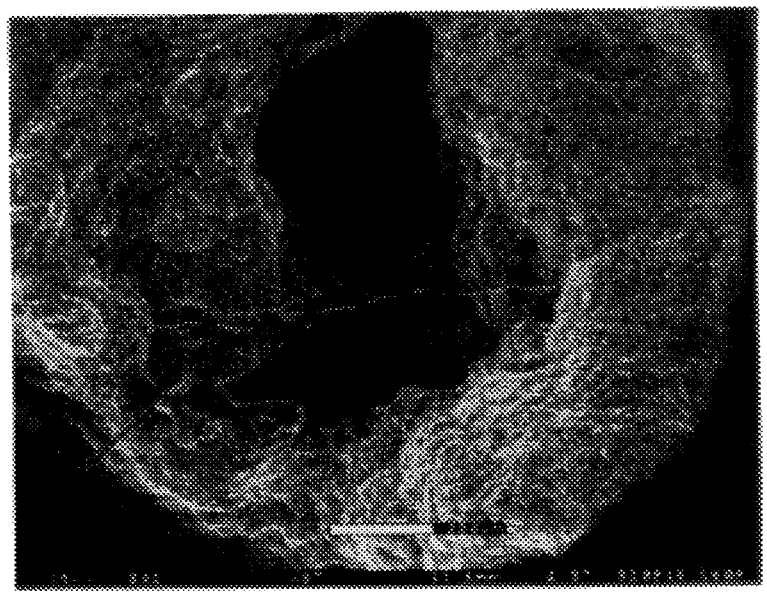
FIG. 6A is an environmental scanning electron micrograph (ESEM) of an untreated blood vessel following trauma.
Figure 6B:
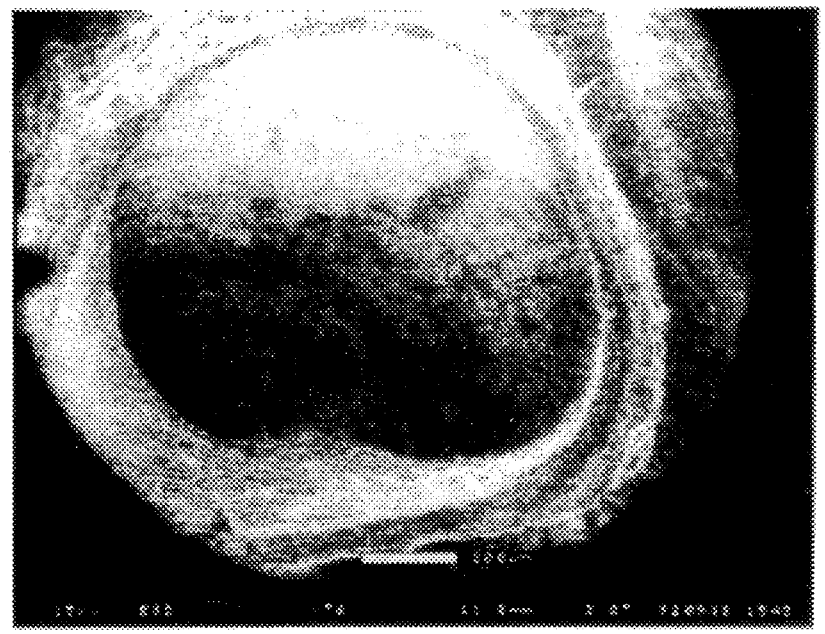
FIG. 6B is an ESEM of a polymer coated blood vessel following trauma.

The treated vessel did not appear colored or different in color after perfusion compared to its color before perfusion, while the untreated control vessel appeared blood red. Thin segments of each vessel were cut from each vessel, were mounted on end, and were examined by environmental scanning electron microscopy (ESEM). ESEM is performed on hydrated samples in relatively low vacuum. This permits the visualization of the polymer film coating in the swollen and wet state. This is important to obtain measurements that may be readily interpreted, since the polymer film is approximately 95% water. A high degree of thrombosis was readily observed in the control vessel. The lumen of this vessel was narrowed to less than one-third its diameter pre-perfusion by the accumulation of thrombus, as shown in FIG. 6A. By contrast, no thrombus could be observed in the lumen of the treated vessel, as shown in FIG. 6B. A higher magnification of the vessel wall demonstrated no adherent thrombus. A still higher magnification shows a white structure which is the polymer film, which is different in contrast from the tissue due to differential charging under the electron beam of the ESEM. The film may be seen to be precisely conformed to the shape of the vessel and be approximately 5-8 μm thick.

The region of polymerization was restricted to the neighborhood of the blood vessel wall surface. The photosensitive dye was adsorbed to the vessel wall. Unbound dye was rinsed away. The entire lumen was filled with prepolymer, but upon illumination the gel formation was restricted to the vessel wall where the dye and the prepolymer meet. This interfacial polymerization process can be conducted to produce surface adherent layers that vary in thickness from less than 7 μm to more than 500 μm.

The above procedure was performed in 8 control rat arteries, and 8 treated arteries, with equivalent light microscopic histological results as described above. As demonstrated by this study, PEG prepolymers can be polymerized upon the lumenal surface of blood vessels. The immediate effect of this modification is to reduce the thrombogenicity of an injured blood vessel surface. This has clear utility in improving the outcome of balloon angioplasty by reducing the thrombogenicity of the vessel and lesion injured by balloon dilation. Another effect of this modification is to be reduce smooth muscle cell hyperplasia. This may be expected for two reasons. First, platelets contain a potent growth factor, platelet-derived growth factor (PDGF), thought to be involved in post-angioplasty hyperplasia. The interruption of the delivery of PDGF itself poses a pharmacological intervention, in that a "drug" that would have been delivered by the platelets would be prevented from being delivered. Thrombosis results in the generation of thrombin, which is a known smooth muscle cell mitogen. The interruption of thrombin generation and delivery to the vessel wall also poses a pharmacological intervention. There are other growth factors soluble in plasma which are known to be smooth muscle cell mitogens. The interruption of thrombin generation and delivery to the vessel wall also poses a pharmacological intervention. Moreover, there are other growth factors soluble in plasma which are known to be smooth muscle cell mitogens. The gel layer is known to present a permselective barrier on the surface of the tissue, and thus the gel layer may reasonably be expected to reduce hyperplasia after angioplasty. The inhibition of thrombosis upon the vessel wall may also reduce the incidence of abrupt reclosure and vasospasm, both of which occur sometimes following vascular intervention.

EXAMPLE 21

Interfacial Polymerization of Macromers Inside Blood Vessels to Prevent Thrombosis Macromer solutions were polymerized interfacially within previously injured blood vessels in vivo to prevent thrombosis. The carotid artery was exposed, and a polyethylene tube (PE-10) was used to cannulate the exterior carotid artery. The artery was clamped with fine arterial clamps proximal to the interior/exterior carotid artery bifurcation and approximately 2 cm distal to the bifurcation. A 1 ml tuberculin syringe was used to rinse the blood from the lumen of the isolated zone by filling and emptying the vessel zone. The vessel was injured by crushing using a hemostat. The isolated zone was filled with a 10 mM solution of eosin Y for 2 minutes, after which it was rinsed and filled with a 20% solution of a macromer in saline with 0.1 mM triethanolamine and 0.15% N-vinyl pyrrolidinone. The macromer consisted of a PEG chain of MW 8,000 daltons, extended on both sides with a lactic acid oligomer of an average degree of polymerization of 5 lactidyl groups, and further acrylated nominally at both ends by reaction with acryloyl chloride. The vessel was illuminated transmurally using an argon ion laser (514 nm) at an intensity of approximately 1 mW/cm$^2$ for 5 seconds. Following this, the cannula was removed from the exterior carotid artery and the artery was ligated at the bifurcation. The arterial clamps were removed to permit the resumption of blood flow. Perfusion was allowed for 20 minutes, following which the vessel were again isolated, removed from the body, gently rinsed, fixed, and prepared for light microscopic histological analysis. Using the naked eye, the crushed segments in control animals, which lacked illumination, were red, indicating internal thrombus with entrapped red blood cells. By contrast, no redness was observed at the site of the crush injury in the treated vessels. Histology showed extensive thrombus, fibrin, and entrapped red blood cells in the non-treated vessels. By contrast, no thrombus or fibrin or entrapped red blood cells were observed in the treated vessels. The procedure was conducted in four control animals and three treated animals.

This example demonstrates that the polymerization can be carried out in situ in the living animal, that the polymer coating remains adherent to the vessel wall during arterial blood flow, and that the polymer coating can prevent thrombosis in vivo in non-anticoagulated animals. This approach to treatment has clear benefits in preventing abrupt reclosure, vasospasm, and restenosis after intravascular interventional procedures. Moreover, it is more generally applicable to other intraluminal and open-surface organs to be treated.

Modifications and variations of the present invention, the macromer and polymeric compositions and methods of use thereof, will be obvious to those skilled in the art from the foregoing detailed description. Such modifications and variations are intended to come within the scope of the appended claims.

We claim:

1. A method of forming a polymeric, biocompatible material on tissue or cells, the method comprising applying to the tissue or cells a solution of biodegradable, polymerizable macromer having a solubility of at least about 1 g/100 ml in an aqueous solution comprising at least one water soluble region, at least one degradable region which is hydrolyzable under in vivo conditions, and free radical polymerizable end groups having the capacity to form additional covalent bonds resulting in macromer interlinking, wherein the polymerizable end groups are separated from each other by at least one degradable region, in the presence of a free radical initiator, and polymerizing the macromer.

2. The method of claim 1 wherein the tissue is coated with the polymerized macromer to inhibit the formation of adhesions.

3. The method of claim 1 wherein the method further comprises applying the macromer solution to tissue surfaces in the presence of free radical initiator and polymerizing the macromer to adhere the tissue surfaces.

4. The method of claim 1 further comprising providing with the macromer solution biologically active materials selected from the group consisting of proteins, carbohydrates, nucleic acids, inorganic biologically active materials, cells, tissues, and tissue aggregates.

5. A method of forming a polymeric, biocompatible material on tissue, the method comprising:
   applying a free radical initiator at a tissue site; and
   applying to the tissue site a solution of biodegradable, polymerizable, and at least substantially water soluble macromer comprising at least one water soluble region, at least one degradable region, and at least two free radical polymerizable regions, wherein the polymerizable regions are separated from each other by at least one degradable region, and polymerizing the macromer in the presence of the free radical initiator.

6. A method of forming a polymeric, biocompatible material on tissue, the method comprising:

applying a free radical initiator to a tissue site, permitting the initiator to bind to the tissue, and removing unbound initiator;

applying to the tissue site, after removal of the unbound initiator, a solution of biodegradable, polymerizable, and at least substantially water soluble macromer comprising at least one water soluble region, at least one degradable region, and at least two free radical polymerizable regions, wherein the polymerizable regions are separated from each other by at least one degradable region, and polymerizing the macromer in the presence of the free radical initiator.

7. The method of claim 1 further comprising providing with the macromer solution biologically active molecules selected from the group consisting of enzymes, antibiotics, antineoplastic agents, local anesthetics, hormones, antiangiogenic agents, antibodies, neurotransmitters, psychoactive drugs, drugs affecting reproductive organs, and antisense oligonucleotides.

8. The method of claim 1 wherein the macromer comprises a water soluble core region, at least two degradable extensions on the core, and an end cap on at least two of the degradable extensions, wherein the core comprises poly(ethylene glycol);

each extension comprises biodegradable poly($\alpha$-hydroxy acid); and each end cap comprises an acrylate oligomer or monomer.

9. The method of claim 8 wherein the poly(ethylene glycol) has a molecular weight between about 400 and 30,000 Da;

the poly($\alpha$-hydroxy acid) oligomer has a molecular weight between about 200 and 1200 Da; and the acrylate oligomer or monomer has a molecular weight between about 50 and 200 Da.

10. The method of claim 1 wherein the degradable region is selected from the group consisting of poly($\alpha$-hydroxy acids), poly(lactones), poly(amino acids), poly(anhydrides), poly(orthoesters), poly(orthocarbonates) and poly(phosphoesters).

11. The method of claim 10 wherein the poly($\alpha$-hydroxy acid) is selected from the group consisting of poly(glycolic acid), poly(DL-lactic acid) and poly(L-lactic acid).

12. The method of claim 10 wherein the poly(lactone) is selected from the group consisting of poly($\epsilon$-caprolactone), poly($\delta$-valerolactone), and poly(gamma-butyrolactone).

13. The method of claim 1 wherein the water soluble region is selected from the group consisting of poly(ethylene glycol), poly(ethylene oxide), poly(vinyl alcohol), poly(vinylpyrrolidone), poly(ethyloxazoline), poly(ethylene oxide)-co-poly(propyleneoxide) block copolymers, polysaccharides, carbohydrates, proteins, and combinations thereof.

14. The method of claim 1 wherein the polymerizable end groups contain a carbon-carbon double bond capable of cross-linking and polymerizing the macromers.

15. The method of claim 1 wherein the macromer is polymerized to form a coating on the tissue thereby to inhibit restenosis.

16. The method of claim 1 wherein the macromer is polymerized to form a coating on the tissue thereby to form a sealant on the tissue.

17. The method of claim 1, wherein the macromer is characterized in that the water soluble region is attached to a degradable region, at least one polymerizable end group is attached to the water soluble region, and at least one polymerizable end group is attached to the degradable region.

18. The method of claim 1, wherein the macromer is characterized in that the water soluble region forms a central core, at least two degradable regions are attached to the core, and at least two polymerizable end groups are attached to the degradable regions.

19. The method of claim 1, wherein the macromer is characterized in that the degradable region is a central core, at least two water soluble regions are attached to the core, and at least one polymerizable end group is attached to each water soluble region.

20. The method of claim 1, wherein the macromer is characterized in that the water soluble region is a macromer backbone, the degradable region is a branch or graft attached to the macromer backbone, and at least two polymerizable end groups are attached to the degradable regions.

21. The method of claim 1, wherein the macromer is characterized in that the degradable region is a macromer backbone, the water soluble region is a branch or graft attached to the degradable backbone, and two or more polymerizable end groups are attached to the water soluble branches or grafts.

22. The method of claim 1, wherein the macromer is characterized in that the water soluble region is a star backbone, the degradable region is a branch or graft attached to the water soluble star backbone, and at least two polymerizable end groups are attached to a degradable branch or graft.

23. The method of claim 1, wherein the macromer is characterized in that the degradable region is a star backbone, the water soluble region is a branch or graft attached to the degradable star backbone, and two or more polymerizable end groups are attached to the water soluble branch or graft.

24. The method of claim 1, wherein the macromer is characterized in that the water soluble region is also the degradable region.

25. The method of claim 1, wherein the macromer is characterized in that the water soluble region is also the degradable region, and one or more additional degradable regions are grafts or branches upon the water soluble region.

26. The method of claim 1 wherein crosslinking and polymerization of the macromer can be initiated by a light-sensitive free-radical polymerization initiator with or without a cocatalyst, further comprising a free radical polymerization initiator.

27. The method of claim 26 wherein the initiator is selected from the group consisting of xanthine dyes, acridine dyes, thiazine dyes, phenazine dyes, camphorquinone dyes, and acetophenone dyes.

28. The method of claim 26 wherein the initiator is selected from the group consisting of an eosin dye with triethanolamine, 2,2-dimethyl-2-phenyl acetophenone, and 2-methoxy-2-phenyl acetophenone.

29. The method of claim 1 wherein crosslinking or polymerizations are initiated in situ by light having a wavelength of 320 nm or longer.

30. The method of claim 1 wherein the initiator is a thermal initiator.

31. The method of claim 1, wherein the initiator further comprises an initiator mixture.

32. The method of claim 1, wherein the polymerized macromer forms a barrier on the cells or tissue.

33. The method of claim 1, wherein the tissue or cell is encapsulated by the polymerized macromer.

34. The method of claim 1, wherein the polymerized macromer comprises a tissue support.

35. The method of claim 34, wherein the support forms a shaped article within the body to serve a mechanical function.

36. The method of claim 35, wherein the support is selected from the group consisting of organ sealants, bone defect sealants, space-fillers for aneurysms, blood vessel interior coatings, vessels, tubes and organ holding strictures.

37. The method of claim 2, for inhibiting adhesions of the peritoneal cavity.

38. The method of claim 1, further comprising providing with the macromer solution biologically active organic molecules.

39. A method of forming a polymeric, biocompatible material on a surface, the method comprising:

applying to the surface a solution of a biodegradable, polymerizable macromer, having a solubility of at least about 1 g/100 ml in an aqueous solution, and comprising at least one water soluble region, at least one degradable region which is hydrolyzable under in vivo conditions, and free radical polymerizable end groups, wherein the polymerizable end groups are separated from each other by at least one degradable region, in the presence of a free radical initiator, and polymerizing the macromer.

40. The method of claim 39 wherein the surface comprises glass.

41. The method of claim 39, further comprising contacting the surface with cells or tissue.

42. The method of claim 41, wherein polymerized macromer forms a coating on the surface which inhibits adhesion to the surface.

43. The method of claim 42 wherein the adhesion of protein, cells or tissue to the surface is inhibited.

* * * * *